US009119784B2

(12) United States Patent
Longenecker

(10) Patent No.: US 9,119,784 B2

(45) Date of Patent: Sep. 1, 2015

(54) METHOD OF TREATING PATIENTS WITH A MUCINOUS GLYCOPROTEIN (MUC-1) VACCINE

(71) Applicant: Oncothyreon Inc., Seattle, WA (US)

(72) Inventor: B. Michael Longenecker, Edmonton (CA)

(73) Assignee: ONCOTHYREON INC., Seattle, WA (US)

( * ) Notice: Subject to any disclaimer, the term of this patent is extended or adjusted under 35 U.S.C. 154(b) by 0 days.

(21) Appl. No.: 14/489,304

(22) Filed: Sep. 17, 2014

(65) Prior Publication Data

US 2015/0071990 A1 Mar. 12, 2015

Related U.S. Application Data

(62) Division of application No. 11/475,250, filed on Jun. 27, 2006, now Pat. No. 8,871,250.

(60) Provisional application No. 60/694,233, filed on Jun. 28, 2005.

(51) Int. Cl.

| | |
|---|---|
| ***A61K 9/127*** | (2006.01) |
| ***A61K 31/675*** | (2006.01) |
| ***A61K 31/739*** | (2006.01) |
| ***A61K 38/17*** | (2006.01) |
| ***A61K 38/20*** | (2006.01) |
| ***A61K 39/00*** | (2006.01) |
| ***C12Q 1/68*** | (2006.01) |
| ***A61K 47/26*** | (2006.01) |

(52) U.S. Cl.

CPC ............... *A61K 9/127* (2013.01); *A61K 31/675* (2013.01); *A61K 31/739* (2013.01); *A61K 38/1735* (2013.01); *A61K 38/2013* (2013.01); *A61K 39/0011* (2013.01); *A61K 39/0012* (2013.01); *A61K 47/26* (2013.01); *C12Q 1/6886* (2013.01); *A61K 2039/55533* (2013.01); *A61K 2039/55555* (2013.01); *A61K 2039/55572* (2013.01); *C12Q 2600/106* (2013.01); *C12Q 2600/112* (2013.01); *C12Q 2600/118* (2013.01); *C12Q 2600/136* (2013.01); *C12Q 2600/156* (2013.01); *C12Q 2600/172* (2013.01)

(58) Field of Classification Search

None

See application file for complete search history.

(56) References Cited

U.S. PATENT DOCUMENTS

| | | | | |
|---|---|---|---|---|
| 4,501,728 | A | 2/1985 | Geho et al. | |
| 4,837,028 | A | 6/1989 | Allen | |
| 4,868,155 | A | 9/1989 | Durette et al. | |
| 5,019,369 | A | 5/1991 | Presant et al. | |
| 5,019,383 | A | 5/1991 | Hopp | |
| 5,580,563 | A | 12/1996 | Tam | |
| 5,744,144 | A | 4/1998 | Finn et al. | |
| 5,837,249 | A | 11/1998 | Heber-Katz et al. | |
| 5,840,839 | A | 11/1998 | Wang et al. | |
| 5,871,746 | A | 2/1999 | Boutillon et al. | |
| 5,910,306 | A | 6/1999 | Alving et al. | |
| 5,993,823 | A | 11/1999 | Boutillon et al. | |
| 6,013,779 | A | 1/2000 | Wong et al. | |
| 6,015,564 | A | 1/2000 | Boutillon et al. | |
| 6,090,406 | A | 7/2000 | Popescu et al. | |
| 6,344,203 | B1 | 2/2002 | Sandrin et al. | |
| 6,600,012 | B1 | 7/2003 | Agrawal et al. | |
| 6,683,052 | B1 | 1/2004 | Thiam et al. | |
| 8,871,250 | B2 * | 10/2014 | Longenecker | 424/450 |
| 2002/0051813 | A1 | 5/2002 | Bonii et al. | |
| 2002/0132771 | A1 | 9/2002 | Madiyalakan | |
| 2003/0157160 | A1 | 8/2003 | Budzynski et al. | |
| 2006/0069238 | A1 | 3/2006 | Koganty et al. | |
| 2007/0014844 | A1 | 1/2007 | Longenecker | |
| 2008/0131495 | A1 | 6/2008 | Longenecker | |

FOREIGN PATENT DOCUMENTS

| | | |
|---|---|---|
| EP | 0093851 | 11/1983 |
| EP | 0203676 | 12/1986 |
| EP | 0230893 | 8/1987 |
| EP | 0491628 | 6/1992 |
| EP | 0945461 | 9/1999 |
| EP | 1065212 | 1/2001 |
| EP | 1182210 | 2/2002 |
| EP | 1896051 | 3/2008 |
| FR | 2776926 | 10/1999 |
| JP | 2001-510440 | 7/2001 |
| WO | WO-93-21211 | 10/1993 |
| WO | WO-95-27505 | 10/1995 |
| WO | WO-96-40236 | 12/1996 |
| WO | WO-97-34921 | 9/1997 |
| WO | WO-97-38010 | 10/1997 |
| WO | WO-98-50527 | 11/1998 |
| WO | WO-01-12217 | 2/2001 |
| WO | WO-01-18035 | 3/2001 |

(Continued)

OTHER PUBLICATIONS

About the Albert B. Sabin Vaccine Institute, Cancer Immunol Immunotherapy 52:S1-S38 (2003).

Alving. Lipopolysaccharde, Lipid A, and Liposomes Containing Lipid a as Immunologic Adjuvants, Immunobiol 187(3-5):430-446 (1993).

Apostolopoulos et al. Induction of HLA-A2 restricted CTLs to the mucin-1 human breast cancer antigen, J Immunol 159:5211-5218 (1997).

Bakker-Woudenberg et al. Liposomes as Carriers of Antimicrobial Agents or Immunomodulatory Agents in the Treatment of Infections, Eur J Clin Microbiol Infect Dis 12(Suppl 1):61-67 (1993).

Bartels et al. Adoptive cellular immunotherapy fo cancer in mice using allogenic T-cells, an Oncology Journal for Surgeons 3:67-73 (1996).

Benmohamed et al. High immunogenicity iin chimpanzees of peptides and lipopeptides dervide from four new plasmodium flaciparum pre-erythrocytic molecules Vaccine 18:2843-2855 (2000).

Benmohamed et al. Lipopeptide immunization without adjuvant induces potent and long-lasting B T helper and cytotoxic T lymphocyte responses against a malaria liver stage antigent in mice and chimpanzees Eur J Immunol 27:1242-1253 (1997).

Brossart et al. Identification of HLA-A2-restricted T-cell epitopes derived from the MUC1 tumor antigen for broadly applicable vaccine therpaies, Blood 93:4309-4317 (1999).

(Continued)

*Primary Examiner* — Michael Burkhart

(74) *Attorney, Agent, or Firm* — Wilson Sonsini Goodrich & Rosati

(57) ABSTRACT

The present invention provides a method for treating an individual who is afflicted with a cancer, such as non-small cell lung cancer or prostate cancer, by administering to that individual a MUC-1-based formulation. The formulation may be a MUC-1 based liposomal vaccine formulation.

24 Claims, 23 Drawing Sheets

(56) References Cited

FOREIGN PATENT DOCUMENTS

| | | |
|---|---|---|
| WO | WO-01-36433 | 5/2001 |
| WO | WO-01-70265 | 9/2001 |
| WO | WO-02-43699 | 6/2002 |
| WO | WO-02-076485 | 10/2002 |
| WO | WO-03-003985 | 1/2003 |
| WO | WO-03-089574 A2 | 10/2003 |
| WO | WO-03-089574 A3 | 10/2003 |
| WO | WO-03-094850 | 11/2003 |
| WO | WO-2005-112546 | 12/2005 |

OTHER PUBLICATIONS

Burchell, et al. Effect of Modification of Carbohydrate Side Chains on the Reactivity of Antibodies with Core-Protein Epitopes of the MUC1 Gene Product, Epith Cell Biol. vol. 2, pp. 155-162, 1993.

Butts et al. A multicenter phase IIB randomized study of liposomal MUC1 vaccine for immunotherapy of non-small cell lung cancer (NSCLC):L-BLP25 non-small cell cancer study group, Ann Onc 15(Suppl.3):1112 (2004) (Abstract).

Butts et al. Randomized phase IIB trial of BLP25 liposome vaccine in stage IIIB and IV non-small cell lung cancer, J Clin Onc 23:6674-6681 (2005).

Butts et al. Updated survival analysis in patients with stage BIB or IV non-smallcell lung cancer receiving BLP25 liposome vaccine (L-BLP25):phase JIB randomized, multicenter, open-label trial. J Cancer Res Clin Oncol, 2011, 137:1337-1342.

Carmon et al. Novel breast-tumor-associated MUC1-derived peptides: characterization in Db-/-X beta 2 microglobulin (beta2m) null mice transgenic for a chimeric HLA-A2. 1/Db microglobulin single chain, Int J Cancer 85:391-397 (2000).

Carrington et al. A comparison of HLA-DR and -DQ allele and haplotype frequencies in Trinidadian populations of African, South Asian, and mixed ancestry, Hum Immunol, 63(11):1045-54 (2002).

CN200680031006.9 Office Action mailed Jan. 11, 2011 (English translation).

Denton et al. Sequential Order of T and B Cell Epitopes Affects Immunogenicity But Not Antibody Recognition of the B Cell Epitope, Peptide Research. 7(5_:258-264. 1994.

Diez-Barra et al. Chemical Abstract, Solvent free phase transfer catalysis. Improvements on serine O-alkylation, Database accesion No. 127:220955 (1997).

Domenech et al. Identification of an HLA-A11-Restricted Epitope from the Tandem Repeat Domain of the Epithelial Tumor Antigen Mucin, J. Immunoil. 1995, 155:4766-4774.

Ellis et al. Frequencies of HLA-A2 alleles in five U.S. population groups. Predominance of A*02011 and identification of HLA-A*0231, 2000, Hum Immunol, 61(3):334-40.

Engelmann et al. Identification and Topology of Variant Sequences within Individual Repeat Domains of the Human Epithelial Tumor Mucin MUC1 The Journal of Biological Chemistry. 276(30):27764-27769, 2001.

EP03721571 Search Report mailed Feb. 28, 2006.

EP05769609.8 Office Action mailed Jun. 1, 2011.

EP06022033.2 Search Report mailed Feb. 12, 2008.

EP06808953.1 Office Action mailed Jun. 29, 2011.

EP06808953.1 Search Report and Opinion mailed Jul. 16, 2008.

EP10191602.1 Examination Report mailed May 8, 2012.

EP10191602.1 Search Report and Opinion mailed Jul. 27, 2011.

Flinn et al. Oral absorption studies of lipidic conjugates of thyrotropin releasig hormone (TRH)-1 and luteinizing hormone-releasing hormone (LHRH), Intl J Pharmaceutics 137:33-39 (1996).

Fung et al. Specific Immunosuppressive Activity of Epiglycanin A Mucin-Like Glycoprotein Secreted by a Murine Mammary Adenocarcinoma TA3-HA, Cancer Research 51(4):1170-1176 (1991).

Gahery-Segard et al. Multiepitopic B- and T-cell responses induced in humans by a human immunodeficiecny virus type 1 lipopeptide vaccine, Journal of Virology 74:1694-1703 (2000).

GCC/P/2006/6506 Examination Report mailed Aug. 1, 2011 (English translation only).

Gendler et al. A highly immunogenic region of a human polymorphic epithelial mucin expressed by carcinoma is made up of tandem repeats, J Biol Chem 263:12820-12823 (1988).

Guan et al. Liposomal formulations of synthetic MUC1 peptides:Effects of encapsulation versus surface display of peptides on immune responses, Bioconjugate Chem. 9:451-458 (1998).

Gupta et al. Adjuvants—a balance between toxicity and adjuvanticity, Vaccine 11:293-306 (1993).

Hanisch, et al. MUC1:the polymorphic appearance of a human mucin, Glycobiology, vol. 10, No. 5, pp. 439-449, 2000.

Hanski et al. Altered glyclosylation of the MUC-1 protein core contributes to the colon carcinoma-associated increase of mucin-bound sialyl-lewis expression, Cancer Research 53:4082-4088 (1993).

Heukamp et al, Identification of three non-VNTR MUC1-derived HLA-A*0201- restricted T-cell epitopes that induce protective anti-tumor immunity in HLA-A2/Kb transgenic mice, Int J Cancer 91:385-392 (2001).

Hiltbold et al. Naturally processed class II epitope from the tumor antigen MUC1 primes human CD4+ T cells, Cancer Res 58:5066-5070 (1998).

JP20085190017 Office Action mailed May 30, 2012 (English Translation only).

Karanikas et al. Antibody and T cell Responses of Patients with Adenocarcinoma Immunized with Mannan-MUC1 Fusion Protein, J Clin Invest 100:2783-2792 (1997).

Karsten et al. Enchanced Biding of Antibodies to the DTR Motif of MUC1 Tandem repeat Peptide is Mediated by Site-specific Glycosylation. Cancer Res 58:2541-2549 (1998).

Keil et al. Towards the Development of Antitumor Vaccines:A Synthetic Conjugate of a Tumor-Associated MUC1 Glycopeptide Antigen and a Tetanus Toxin Epitope. Angew Chem. Int. Ed. 40(2):366-369, 2001.

Kim. Liposomes as Carriers of Cancer Chemotherapy. Drugs 46(4):579-794 (1993).

Kirschenbaum et al. MUC1 expression in prostate carcinoma:correlation with clinical grade and stage. Molecular Urology 3:163-167 (1999).

Kreuter. Colloidal drug delivery systems, Drugs and Pharmaceutical Sciences, 66:4 pages (1994).

Kudryashov et al. Toward optimized carbohydrate-based anticaner vaccines:eptiope clustering, carrier structure, and adjuvant all influence antibody responses to Lewis conjugates in mice, PNAS 98:3264-3269 (2001).

Lopes et al. Immunoexpression of MUC1 in prostate adenocarcinoma, Virchows Arch 435:330 (1999).

Machy et al. Liposomes in cell biology and pharmacology. 4 pages, John Libbey 1987.

MacLean et al. Prognostic significance of preimmunotherapy serum CA27.29 (MUC-1) mucin level after active specific immunotherapy of metastatic adenocarcinoma patients, J Immunotherapy 20:70-78 (1997).

Martinon et al. Immunization of mice with lipopeptides bypasses the prerequisite for adjuvant, J Immunol 149:3416-3422 (1992).

Mehta et al. L-BLP25 Vaccine plus Letrozole Induces a TH1 Immune Response and has Additive Antitumor Activity in MUC-1 Expressing Mammary Tumors in Mice. Clin Cancer Res. Mar. 20, 2012. 18:2861-2871.

Meylan et al. Atom/fragment contribution method for estimating octanol-water partition coefficients. J Pharm Sci 84:83-92 (1995).

Miller et al. Vaccination of rhesus monkeys with synthetic peptide ina fusogenicproteoliposome elicits simian immunodeficiency virus-specific CD8+ cytotoxic T lymphocytes, J Exp Med 176:1739-1744 (1992).

Moller et al. NMR-based determination of the binding epitope and conformational analysis of MUC-1 glycopeptides and peptides bound to the breast cancer-selective monoclonal antibody SM3, Eur J Biochem 269:1444-1455 (2002).

Morse. Technology Evaluation:BLP-25, Biomira Inc. Curr. Opin. Mol. Ther. Feb. 2001. 3(1):102-105.

Mortara et al. Selection of Virus Variants and Emergence of Virus Escape Mutants after Immunization with an Epitope Vaccine. J Virol 72(2):1403-1410 (1998).

(56) References Cited

OTHER PUBLICATIONS

Mountain. Revisions in the international system for staging lung cancer. Chest 111:1710-1717 (1997).
Murray et al. A Liposomal MUC1 Vaccine for Treatment of Non-Small Cell Lung Cancer (NSCLC); Updated Survival Results from Patients with stage IIIB Disease. Journal of Clinical Oncology, 2005 ASCO Annual Meeting Proceedings. 23(16S, Part 1 of 2):7037 (Jun. 1 Supplement).
Neurath et al. Antibodies to hepatitis B surface antigen (HbsAg) elcited by immunization with a syntetic peptide covalently linked to liposomes, Journal of General Virology 65:1009-1014 (1984).
Ng et al. Prognostic significance of increased immunodetectable MUC-1 in prostate cancer, Proceedings of the American Associaiotn for Cancer Research 38:542 (1997).
North et al. Vaccination with BLP25 liposome vaccine to treat non-small cell lung and prostate cancers. Expert Rev Vaccines 4(3):249-257 (2005).
Ostro et al. Use fo liposomes as injectable drug delivery systems, American Journal of Hospital Pharmacy 46:1576-1587 (1989).
Palmer et al. A phase I/II trial of BLP25 liposomal vaccine for active specific immunotherapy of stage IIIB and IV non-small cell carcinoma of the lung. 2000. Ann. Oncol. 11(suppl. 4):42.
Palmer et al. Phase I Study of the BLP25 (MUC1 Peptide) Liposomal Vaccine for Active Specific Immunotherapy in Stage IIIB/IV Non-Small Cell Lung Cancer,Clinical Lung Cancer 3(1):49-57 (2001).
Pantuck et al. Phase I Trial of Antigen-Specific Gene Therapy Using a Recombinant Vacinia Virus Encoding MUC-1 and IL-2 in MUC-1-Positive Patients with Advanced Prostate Cancer, J Immunother 27(3):240-253 (2004).
Papadopoulos et al. Tumor Angiogenesis is associated with MUC1 overexpression and loss of prostate-specific antigen expression in prostate cancer, Clin Cancer Res 7:1533-1538 (2001).
PCT/IB02/02188 IPRP mailed Jul. 18, 2005.
PCT/IB02/02188 Search Report mailed Dec. 16, 2002.
PCT/IB06/02771 IPRP and Written Opinion mailed Jan. 10, 2008.
PCT/IB06/02771 Search Report mailed Feb. 27, 2007.
PCT/US03/10750 Search Report mailed Jul. 20, 2005.
Petrakou et al. Epitope mapping of anti-MUC1 mucin protein core monoclonal antibodies. Tumor Biol 19:21-29 (1998).
Pihl et al. Mucinous colorectal carcinoma:Immunopathology and prognosis. Pathology 12:439-447 (1980).
Price et al. Summary report on the ISOBM TD-4 workshop: analysis of 56 monoclonal antibodies against the MUC1 mucin, Tumor Biol 19:1-20 (1998).
Reddish et al. Pre-Immunotherapy Serum CA27, 29 (MUC-1) Mucin Level and CD69+ Lmphocytes Correlate with Effects of Theratope Sialyl-TN-KLH Cancer Vaccine in Active Specific Immunotherapy, Cancer Immunology and Immunotherapy 42(5):303-309 (1996).
Reichel et al. Synthetic carbohydrates-based vaccines: synthesis of an L-glycero-D-manno-heptose antigen-T-epitope-lipopeptide conjugate. Chem Comm 2087-2088 (1997).
Samuel. PLGA Nanosphere Delivery of Peptides and Lipopeptides to Dentritic Cells. Cancer Immunol Immunotherapy 52(Suppl):S15 (2002).
Sangha et al. L-BLP25:a peptide vaccine strategy in non-small cell lung cancer. Clin Cancer Res 13:4652s-4654s (2007).
Sauzet et al. Long-lasting anti-viral cytotoxic T lymphocytes induced in vivo with chimeric-multiresticted lipopeptides. Vaccine 13:1339-1345 (1995).
Scher et al. Post-therapy Serum Prostate-Specific Antigen Level and Survival in Patients with Androgen-Independent Prostate Cancer. J National Cancer Institute 91(3):244-251 (1999).
Scherphof et al. Uptake and intracellular processing of targeted and nontargeted liposomes by rat Kupffer cells in viov and in vitro. Annals New York Academy of Sciences 369-385 (1985).
Scholfield et al. MUC1 mucin in urological malignancy. BJU Intl 91:560-566 (2003).
Schut et al. MUC1 expression, splice variant and short form transcription (MUC1/Z, MUC1/Y) in prostate cell lines and tissue. BJU Intl 91(3):278-283 (2003).
Sculier et al. A randomised phase III trial comparing consolidation treatment with further chemotherapy to chest irradiation in patients with initially unresectable locoregional non-small-cell lung cancer responding to induction chemotherapy. European Lung Cancer Working Party. Annals of oncology. 1999. 10(3):295-303.
Seth et al. Evaluation of a Lipopeptide Immunogen as a Therapeutic in HIV Type 1-Seropositive Individuals, Aids Res Human Retroviruses 16(4):337-343 (2000).
Soares et al. Three Different Vaccines Based on the 140-Amino Acid MUC1 Peptide with Seven Tandemly Repeated Tumor-Specific Epitopes Elicit Distinct Immune Effector Mechanisms in Wild-Type Versus MUC1-Transgenic Mice with Different Potential for Tumor Rejection. J Immunol 166:6555-6563 (2001).
Springer et al. T and Tn, general carcinoma autoantigens. Science 224:1198-1206 (1984).
Sugiura et al. Prognostic Value of Pleural Effusion in Patients with Non-Small Cell Lung Cancer. Clinical Cancer Research. 1999. 3:47-50.
Taylor-Papadimitriou et al. Molecular aspects of mucin, Cancer Rev 11-12:11-24 (1988).
Timmerman, Luke. Oncothyreon Marches on With ‘Son of Stimuvax’ Cancer Vaccine. www.Xconomy.com [online], Apr. 10, 2012 [retrieved on Apr. 12, 2012]. Retrieved from the Internet: http://www.xconomy.com/seattle/2012/04/10/oncothyreon-marches-on-with-son-of-stimuvax-cancer-vaccine/.
Toyokuni et al. Synthetic vaccines:synthesis of a dimeric Tn antigen-lipopeptide conjugate that elicits immune responses against Tn-expressing glycoproteins. J Am Chem Soc 116:395-396 (1994).
Tsunoda et al. Lipopeptide particles as the immunologically active component of CTL inducing vaccines, Vaccine 17:675-685 (1999).
TW094110256 Search Report mailed Mar. 29, 2011.
TW95123235 Office Action dated Jan. 16, 2012 (English translation).
Vitiello et al. Development of a lipopeptide-based therapeutic vaccine to treat chronic HBV infection, The Journal of Clinical Investigation Jan. 1995 pp. 341-349.
Von Mendsdorff-Pouilly et al. “Survival in Early Breast Cancer Patients is Favorably Influenced by a Natural Humoral Immune Response to Polymorphic Epithelial Mucin,” J Clin Oncol 18(3):574-583 (2000).
Von Mensdorff-Pouilly et al. Human MUC1 mucin:a multifaceted glycoprotein. Int J Biol Markers 15(4):343-356 (2000) Abstract Only.
Von Mensdorff-Pouilly, et al. Reactivity of Natural and Indiced Human Antibodies to MUC1 Mucin with MUC1 Peptides and N-Acetylgalactosamine (GALNAc) Peptides. Int. J. Cancer 86:702-712. 2000.
Wassef et al. Liposomes as carriers for vaccines, Immunomethods 4:217-222 (1994).
Wilikinson et al. Synthesis and in vitro T-cell immunogenicity of conjugates with dual specificity: attachment of epitope peptides of 16 and 38 kDa proteins from Mycobacterium tuberculosis to branched polypeptide. Bioconjugate Chemistry. 1998. 9(5):539-547.
Zeng et al. Synthesis of a New Template with a Built-in Aduvant and Its Use in Constructing Peptide Vaccine Candidates Through Polyoxime Chemistry. J. Peptide Science, 2:66-72. 1996.
Zhou et al. Antigen Delivery to Mucosa-associated Lymphoid Tissues Using Liposomes as a Carrier. Bioscience Reports. 22(2):355-369. Apr. 2002.

* cited by examiner

| | | | N | % |
|---|---|---|---|---|
| VISIT | GROUP | CA27.29 | | |
| A. PRE | BLP25 | NORMAL | 63 | 37.95 |
| | | ABNORMAL | 21 | 12.65 |
| | CONTROL | NORMAL | 61 | 36.75 |
| | | ABNORMAL | 21 | 12.65 |
| B. POST8 | BLP25 | NORMAL | 62 | 40.52 |
| | | ABNORMAL | 20 | 13.07 |
| | CONTROL | NORMAL | 53 | 34.64 |
| | | ABNORMAL | 18 | 11.76 |

FIG. 4

| HLA TYPE | N TOTAL | LOG-RANK P | COX P | N BLP25 | MEDIAN SURVIVAL (MONTHS) BLP25 | N CONTROL | MEDIAN SURVIVAL (MONTHS) CONTROL |
|---|---|---|---|---|---|---|---|
| A01 | 45 | 0.6482 | 0.5197 | 19 | 10.4 | 26 | 15.4 |
| A02 | 80 | 0.0067 | 0.0063 | 44 | 22.0 | 36 | 11.9 |
| A03 | 37 | 0.9661 | 0.8780 | 22 | 14.8 | 15 | 15.6 |
| A24 | 34 | 0.9930 | 0.9053 | 19 | 11.1 | 15 | 13.0 |
| A11 | 27 | 0.0872 | 0.0760 | 11 | 21.3 | 16 | 11.2 |
| B07 | 35 | 0.5329 | 0.6015 | 22 | 15.1 | 13 | 14.8 |
| B08 | 37 | 0.3208 | 0.1925 | 19 | 9.4 | 18 | 16.0 |
| B44 | 38 | 0.3919 | 0.2835 | 19 | 13.4 | 19 | 11.1 |
| CW07 | 85 | 0.9831 | 0.9865 | 45 | 12.6 | 40 | 13.6 |
| DQB1-06 | 78 | 0.3267 | 0.3850 | 40 | 21.3 | 38 | 14.8 |
| DQB1-02 | 64 | 0.1465 | 0.0424 | 31 | 9.8 | 33 | 16.0 |
| DRB1-04 | 45 | 0.0076 | 0.0043 | 22 | 22.0 | 23 | 11.8 |
| DQB1-05 | 52 | 0.0143 | 0.0213 | 25 |  | 27 | 12.9 |
| DRB1-15 | 45 | 0.2902 | 0.3331 | 25 | 21.3 | 20 | 12.8 |
| DQB1-03 | 42 | 0.7678 | 0.7122 | 23 | 17.1 | 19 | 15.1 |
| DRB1-07 | 40 | 0.5436 | 0.8318 | 19 | 27.6 | 21 | 14.8 |
| DRB1-13 | 37 | 0.7260 | 0.7446 | 19 | 13.4 | 18 | 13.7 |
| DRB3 | 98 | 0.7485 | 0.7871 | 56 | 15.1 | 42 | 14.8 |
| DRB4 | 87 | 0.0505 | 0.1097 | 45 | 17.6 | 42 | 12.4 |
| DRB5 | 47 | 0.1405 | 0.1771 | 25 | 21.7 | 22 | 12.8 |

FIG. 11

| HLA TYPE | N POS BLP | N NEG BLP | LOG-RANK BLP | COX P BLP | MEDIAN SURVIVAL* POS, BLP | MEDIAN SURVIVAL* NEG, BLP | N POS CONTROL | N NEG CONTROL | LOG-RANK CONTROL | COX P CONTROL | MEDIAN SURVIVAL* POS, CONTROL | MEDIAN SURVIVAL* NEG, CONTROL |
|---|---|---|---|---|---|---|---|---|---|---|---|---|
| A01 | 19 | 69 | 0.0569 | 0.6833 | 10.4 | 21.7 | 26 | 57 | 0.9522 | 0.1979 | 15.4 | 12.9 |
| A02 | 44 | 44 | 0.0444 | 0.4514 | 22.0 | 14.1 | 36 | 47 | 0.2531 | 0.1674 | 11.9 | 15.6 |
| A03 | 22 | 66 | 0.4581 | 0.6820 | 14.8 | 17.4 | 15 | 68 | 0.6390 | 0.2100 | 15.6 | 12.8 |
| A11 | 11 | 77 | 0.4693 | 0.7931 | 21.3 | 16.7 | 16 | 67 | 0.2544 | 0.2094 | 11.2 | 14.8 |
| A24 | 19 | 69 | 0.1010 | 0.8378 | 11.1 | 17.6 | 15 | 68 | 0.8730 | 0.2020 | 13.0 | 13.1 |
| B07 | 22 | 66 | 0.8057 | 0.7142 | 15.1 | 17.4 | 13 | 70 | 0.7792 | 0.2076 | 14.8 | 13.0 |
| B08 | 19 | 69 | 0.0290 | 0.7368 | 9.4 | 21.3 | 18 | 65 | 0.5811 | 0.2304 | 16.0 | 12.6 |
| B44 | 19 | 69 | 0.5321 | 0.7242 | 13.4 | 17.5 | 19 | 64 | 0.3133 | 0.1427 | 11.1 | 14.4 |
| CW07 | 45 | 43 | 0.0186 | 0.8470 | 12.6 | 24.2 | 40 | 43 | 0.9509 | 0.1829 | 13.6 | 12.6 |
| DQB1-02 | 31 | 57 | 0.0068 | 0.2849 | 9.8 | 21.7 | 33 | 50 | 0.1359 | 0.1752 | 16.0 | 12.4 |
| DQB1-03 | 23 | 69 | 0.9290 | 0.6334 | 17.1 | 17.5 | 19 | 64 | 0.3966 | 0.2273 | 15.1 | 12.8 |
| DQB1-05 | 25 | 63 | 0.0920 | 0.8384 |  | 16.7 | 27 | 56 | 0.3468 | 0.1833 | 12.9 | 13.3 |
| DQB1-06 | 40 | 48 | 0.5864 | 0.7416 | 21.3 | 16.7 | 38 | 45 | 0.3589 | 0.1510 | 14.8 | 12.5 |
| DRB1-03 | 12 | 76 | 0.0009 | 0.6349 | 9.2 | 21.3 | 11 | 72 | 0.9332 | 0.1915 | 16.0 | 13.0 |
| DRB1-04 | 22 | 66 | 0.1212 | 0.5386 | 22.0 | 16.7 | 23 | 60 | 0.1826 | 0.1568 | 11.8 | 14.3 |
| DRB1-07 | 19 | 69 | 0.6593 | 0.7925 | 27.6 | 16.8 | 21 | 62 | 0.5481 | 0.1381 | 14.8 | 12.8 |
| DRB1-13 | 19 | 69 | 0.7748 | 0.7546 | 13.4 | 17.4 | 18 | 65 | 0.8873 | 0.1921 | 13.7 | 13.0 |
| DRB1-15 | 25 | 63 | 0.9946 | 0.7557 | 21.3 | 16.8 | 20 | 63 | 0.7800 | 0.1939 | 12.8 | 13.6 |
| DRB3 | 56 | 32 | 0.6380 | 0.5614 | 15.1 | 17.6 | 42 | 41 | 0.2215 | 0.2449 | 14.8 | 12.5 |
| DRB4 | 45 | 44 | 0.3283 | 0.6129 | 17.6 | 16.7 | 42 | 41 | 0.3763 | 0.2280 | 12.4 | 14.8 |
| DRB5 | 25 | 63 | 0.3434 | 0.7471 | 21.7 | 15.1 | 22 | 61 | 0.9754 | 0.1950 | 12.8 | 13.6 |

FIG. 16

METHOD OF TREATING PATIENTS WITH A MUCINOUS GLYCOPROTEIN (MUC-1) VACCINE

CROSS-REFERENCE

This non-provisional application claims priority to U.S. patent application Ser. No. 11/475,250, filed Jun. 27, 2006, which claims the benefit of U.S. Provisional Application Ser. No. 60/694,233, filed on Jun. 28, 2005, all of which are incorporated herein in their entireties by reference.

FIELD OF THE INVENTION

The present invention relates to a method for identifying individuals with cancer that are suitable for treatment with a mucinous-glycoprotein (MUC-1)-based formulation. Examples of such cancers are non-small cell lung cancer and prostate cancer. In some cases, the MUC-1-based formulation is a BLP25 vaccine.

BACKGROUND OF THE INVENTION

Lung cancer is the leading cause of cancer-related mortality for both sexes in North America. In 2004, approximately 174,000 new cases of lung cancer (54% in men, 46% in women) were diagnosed in the U.S. Moreover, in 2004 approximately 160,000 people died of this disease in the U.S. alone.

Unfortunately, at the time of diagnosis, only 25% of lung cancer patients are potentially curable by surgery. Furthermore, chemotherapy has only modestly improved the chances of survival in individuals afflicted with the cancer.

Non-small cell lung cancer (NSCLC) is the most common of lung cancers, as it accounts for approximately 75 to 80% of all primary lung cancers. NSCLC is typified by squamous cell carcinoma, adenocarcinoma, and large cell carcinoma. It has been observed that the mucinous glycoprotein, MUC-1, is highly expressed in such carcinomas, beyond levels of normal expression in epithelial cells of healthy individuals. It has also been observed that many carbohydrate moieties that adorn the MUC-1 protein are shorter than those moieties attached to MUC-1 proteins of normal cells, by virtue of attachment to the MUC-1 polypeptide backbone. Thus, the MUC-1 polypeptide backbone in cancer cells is more exposed than the polypeptide backbone in normal cells.

After lung cancer, prostate cancer is the second most common diagnosed cancer in men in the United States. Roughly 190,000 men are diagnosed with prostate cancer in the United States and nearly 30,000 men die from the disease yearly.

Biochemical failure after prostatectomy (PR) for treatment of prostate cancer is often a harbinger of clinical failure, which may shorten the life expectancy of the patient. And although a need exists for additional non-invasive methods of treating prostate cancer, a special need exists for a treatment of men with post-prostatectomy biochemical failure.

There is a need in the art for identifying patients suitable for novel cancer therapies, as well as the development of such novel cancer therapies. The present invention provides a method for identifying individuals with cancer that are suitable for treatment with a mucinous-glycoprotein (MUC-1)-based formulation.

SUMMARY OF THE INVENTION

The present invention relates to the identification and treatment of individuals with cancer, wherein the cancer is suitable for treatment with a MUC-1-based formulation. Examples of such cancers are NSCLC and prostate cancer. The present invention also encompasses the treatment of other cancers in addition to NSCLC and prostate cancer with the described MUC-1-based formulations.

In one embodiment of the invention, the MUC-1-based formulation may be a MUC-1-based liposomal vaccine. For instance, the liposomal vaccine may comprise a MUC-1 peptide in its lipid bilayer or encapsulated within its vesicle structure. The MUC-1 peptide also may be lipidated to facilitate its association with the liposomal lipid bilayer or membrane. The MUC-1 peptide may comprise the amino acid sequence depicted in SEQ ID NO. 1 or an immunologically active fragment or variant thereof (collectively referred to as a "functional variant"), or SEQ ID NO. 2, or an immunologically active fragment or variant thereof. Particular characteristics of MUC-1 core repeat variants are described below.

In another aspect of the present invention, a method ("Method 1") is provided for treating a subject with NSCLC or prostate cancer. The method comprises: (A) selecting for treatment a subject who has NSCLC or prostate cancer, and (B) administering to that subject, for a period of time, a MUC-1-based formulation. In one embodiment of Method 1, the MUC-1 based formulation comprises a liposome that contains at least one polypeptide having the amino acid sequence depicted in SEQ ID NO. 1 or an immunologically active fragment or variant thereof, or SEQ ID NO. 2, or an immunologically active fragment or variant thereof.

In specific embodiments, Method 1 may further include a step (C) comprising evaluating the treated subject. In individual embodiments, evaluating the treated subject may be accomplished by measuring an immune reaction in the treated subject. In certain embodiments, measuring the immune reaction in the treated subject can comprise measuring a T-cell proliferation. In yet other embodiments, evaluating the treated subject can comprise determining at least one or more of: (a) tumor size, (b) tumor location, (c) nodal stage, (d) growth rate of the NSCLC or prostate cancer, (e) survival rate of the subject, (f) changes in the subject's lung cancer or prostate cancer symptoms, (g) changes in the subject's PSA concentration, (h) changes in the subject's PSA concentration doubling rate, (i) changes in the subject's quality of life, or (j) a combination thereof.

In these embodiments, evaluating the subject may be performed before, during, or after the period of time. Evaluating the subject may also be performed before and after the period of time.

In a further embodiment, the formulation is a BLP25 liposome vaccine. "BLP25" is a specific lipidated MUC-1 core repeat, identified below. The BLP25 vaccine may comprise preformed liposomes that comprise a MUC-1 core repeat, such as those depicted in SEQ ID NOs: 1 and 2. The preformed liposomes comprising a MUC-1 core repeat may be lyophilized.

In one embodiment of this method, the BLP25 liposome vaccine is in a kit and instructions for preparing and using the vaccine are included in the kit. Hence, the kit may comprise another liquid, such as a sodium chloride solution (0.9%, USP) that can be used to reconstitute that lyophilized material. Alternatively, the BLP25 liposome vaccine may be supplied as a liquid. The kit also may comprise an adjuvant, or a combination of adjuvants. Examples of adjuvants include, but are not limited to, lipid A, muramyl dipeptide, alum, or a cytokine. Thus, the kit may comprise a number of vials or vessels that enable a person to prepare the BLP25 vaccine for administration.

The step of administering the formulation to the subject may be by any suitable method, and utilizing any pharmaceutically acceptable dosage form. Examples of administration methods include, but are not limited to, injection, wherein the injection is an intramuscular injection, a subcutaneous injection, intravenous, intranodal, intratumoral, intraperitoneal, or an intradermal injection. Alternatively, the vaccine or the liposomally-bound MUC-1 core repeat peptide may be administered by aerosol, nasal, oral, vaginal, rectal, ocular, local (powders, ointments or drops), buccal, intracisternal, intraperitoneal, or topical administration, and the like. The vaccine or the liposomally-bound MUC-1 core repeat peptide also may be administered via a formulation suitable for transdermal delivery, such as via a transdermal patch.

In yet another aspect of the present invention, described is a method ("Method 2") for improving or maintaining the quality of life of an individual with cancer, such as NSCLC or prostate cancer. This method may comprise administering to a subject diagnosed with a cancer susceptible to treatment with a MUC-1 based formulation, such as NSCLC or prostate cancer, a dose of BLP25 liposome vaccine routinely for a period of time. In a further aspect of Method 2, a combined score of the individual's physical well-being, functional well-being, and cancer symptoms before, during, and after a period of time may be calculated.

In one embodiment, the dose of BLP25 liposome vaccine provides about 1,000 μg of the BLP25 MUC-1 lipopeptide, in one or multiple administrations, although other doses, described below, may be administered. See, for instance, the doses envisioned under the BLP25 Dosages subsection below.

Another aspect of the present invention is a method for identifying subjects suitable for treatment with a MUC-1-based composition, such as a BLP25 vaccine. One embodiment of the method entails determining whether the level of circulating MUC-1 peptide in a subject's bloodstream, or in a blood, plasma, urine, serum, or other suitable biological sample, is normal or abnormal. If the level of circulating MUC-1 is normal, then the subject is suitable for subsequent treatment with a MUC-1 composition. That is, a subject having a normal level of circulating MUC-1 can be given a dose of a MUC-1 vaccine, such as BLP25. In one embodiment, the upper limit of the normal level of circulating MUC-1 is about 37.7 U/ml. Accordingly, a subject having a circulating MUC-1 level of 37.7 U/ml or less is suitable for treatment with a MUC-1 composition, such as a BLP25 vaccine. However, it is well within the purview of the skilled person to determine threshold levels of circulating MUC-1 peptides in different groups of individuals. That is, the value "37.7 U/ml" is not necessarily a definitive threshold for all assayable populations. A "normal" quantity of circulating antigen can be determined from a desired subpopulation and used as an indicator to classify MUC-1 quantities as either normal or abnormal.

In another embodiment, the method entails detecting the presence of HLA A2 protein or encoding nucleic acid or an HLA A2 RNA transcript in a subject's bloodstream, or in a blood, plasma, urine, serum, or other suitable biological sample. Detection of the presence of HLA A2 protein or encoding nucleic acid or an HLA A2 RNA transcript in the biological sample indicates that the subject is suitable for treatment with a MUC-1 based composition, such as a BLP25 vaccine.

In one embodiment, the subject screened for suitability for treatment with a MUC-1 composition has stage IIIB or stage IV non-small cell lung cancer.

In one aspect of the present invention is a method for treating a subject with cancer. This method comprises (a) selecting for treatment a subject having a cancer cell that expresses MUC-1, and (b) administering to that subject, for a period of time, a MUC-1-based formulation, wherein the formulation comprises: (i) a liposome; and (ii) at least one polypeptide comprising the amino acid sequence selected from the group consisting of the amino acid sequence of SEQ ID NO. 1, an immunologically active variant of the amino acid sequence of SEQ ID NO. 1, the amino acid sequence of SEQ ID NO. 2, and an immunologically active variant of the amino acid sequence of SEQ ID NO. 2, and wherein the subject does not have a high level of circulating MUC-1 in the subject's serum. In one embodiment, the cancer is selected from the group consisting of ovarian cancer, liver cancer, colon cancer, breast cancer, pancreatic cancer, kidney cancer, head and neck cancer, and multiple myeloma.

Both the foregoing general description and the following brief description of the drawings are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 4 is a table listing the frequency distribution of patient CA27.29 values by visit, arm (BLP25 or Control), and normal/abnormal level.

FIG. 11 illustrates the survival analyses that were performed for the chosen HLA types between treatment arms.

FIG. 16 illustrates additional survival analyses within the treatment arms for the same haplotypes listed in FIG. 11.

DETAILED DESCRIPTION OF THE INVENTION

Figure 1:
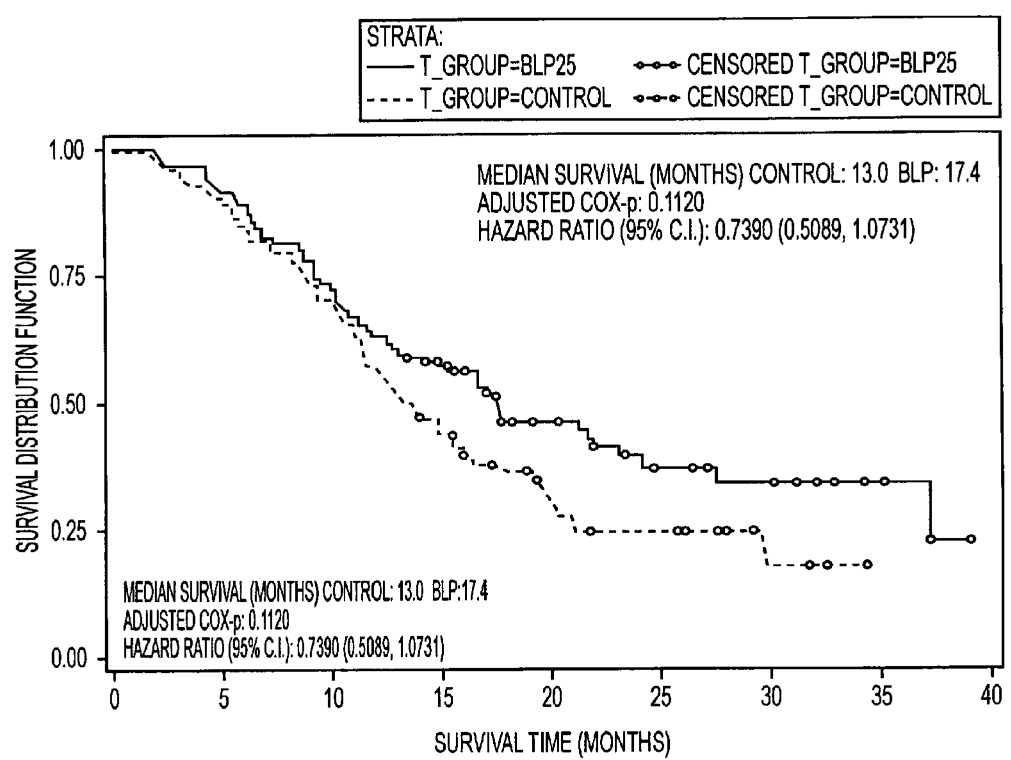
FIG. 1 is a graph depicting the results from a study, detailed herein, showing the overall survival by study arm between patients receiving treatment with BLP25 liposomal vaccine or patients receiving only best supportive care (BSC). See example 1 below.

The present invention provides MUC-1 based formulations and methods for treating an individual who is afflicted with cancer, wherein the cancer is susceptible to treatment with a MUC-1 formulation. Examples of such cancers are NSCLC and prostate cancer. The present invention also encompasses the treatment of other cancers in addition to NSCLC and prostate cancer with the described MUC-1-based formulations.

According to the present invention, a formulation may comprise a MUC-1 core repeat. A MUC-1 core repeat may be a sequence of amino acids that occurs any number of times in a MUC-1 protein. Preferably, a MUC-1 core repeat peptide of the present invention mimics the exposed nature of a MUC-1 protein expressed in cancer cells, which have shorter carbohydrate moieties attached to the MUC-1 protein backbone.

In one embodiment, a MUC-1 core repeat of the present invention has the amino acid sequence, STAPPAHGVTSAPDTRPAPGSTAPP (SEQ ID NO. 1).

A MUC-1 core repeat may also have the amino acid sequence depicted in any of the following:

```
                                        (SEQ ID NO: 2)
STAPPAHGVTSAPDTRPAPGSTAPPK(palmitoyl)G

                                        (SEQ ID NO: 3)
STAPPAHGVTSAPDTRPAPG
```

In certain embodiments, this core repeat may be lipidated. One such MUC-1 core repeat lipopeptide is referred to herein as BLP25. The formulation may also be associated with a liposome. This association may include, but is not limited to, incorporation of the peptide into the liposome or encapsulation of the peptide by the liposome.

A liposome vaccine that contains a BLP25 lipopeptide is referred to herein as "L-BLP25."

The formulations of the invention may further comprise an adjuvant, or a combination of adjuvants, such as lipid A or interleukin-2 (IL-2). Other exemplary adjuvants useful in the invention are described below. The MUC-1-based formulation may be formulated as a vaccine, and the vaccine may be a liposomally-associated MUC-1 core repeat vaccine. In several embodiments, the vaccine formulation comprises a liposomally-associated MUC-1 core repeat and an adjuvant. The MUC-1 core repeat can be lipidated.

A vaccine of the present invention may comprise: (a) a MUC-1 core repeat comprising the sequence of SEQ ID NO.: 1 and exogenous lipid; or (b) a MUC-1 core repeat comprising the sequence of SEQ ID NO.: 1 and a liposome; or (c) a MUC-1 core repeat comprising the sequence of SEQ ID NO.: 1 and a liposome and an adjuvant; or (d) a MUC-1 core repeat comprising the sequence of SEQ ID NO.: 1 and a liposome and an adjuvant, where the adjuvant is lipid A.

In certain other embodiments, a vaccine of the present invention may comprise (a) a MUC-1 core repeat comprising the sequence of SEQ ID NO.: 2 and exogenous lipid; or (b) a MUC-1 core repeat comprising the sequence of SEQ ID NO.: 2 and a liposome; or (c) a MUC-1 core repeat comprising the sequence of SEQ ID NO.: 2 and a liposome and an adjuvant; or (d) a MUC-1 core repeat comprising the sequence of SEQ ID NO.: 2 and a liposome and an adjuvant, where the adjuvant is lipid A.

The concept of treating individuals having a cancer susceptible to treatment with a MUC-1-based formulation, such as NSCLC or prostate cancer, as well as the constituents of the MUC-1-based vaccine formula, are described in more detail below.

I. BLP25 Liposome Vaccine

In one embodiment, the MUC-1-based formulation comprises a certain amount of MUC-1 lipopeptide BLP25 and a certain amount of adjuvant. Such a formulation is referred to herein as a BLP25 Liposome Vaccine ("L-BLP25"), which may be in a liquid or lyophilized formulation. For instance, the formulation or vaccine may contain, in a single dosage amount, about 1000 μg of MUC-1 lipopeptide BLP25 and about 500 μg of lipid A.

Other microgram amounts of MUC-1 lipopeptide and lipid A, however, are envisioned in this invention. For instance, the amount of BLP25 lipopeptide may be sufficient to accommodate multiple doses of the vaccine. Hence, the MUC-1 core repeat formulation may contain, for example, about 50 μg, about 100 μg, about 200 μg, about 300 μg, about 400 μg, about 500 μg, about 600 μg, about 700 μg, about 800 μg, about 900 μg, about 1,000 μg, about 1,010 μg, about 1,020 μg, about 1,030 μg, about 1,040 μg, about 1,050 μg, about 1,060 μg, about 1,070 μg, about 1,080 μg, about 1,090 μg, about 1,100 μg, about 1,200 μg, about 1,300 μg, about 1,400 μg, about 1,500 μg, about 1,600 μg, about 1,700 μg, about 1,800 μg, about 1,900 μg, about 2,000 μg, about 3000 μg, about 4000 μg, about 5000 μg, about 6000 μg, about 7000 μg, about 8000 μg, about 9000 μg, about 10000 μg, about 15000 μg, about 25000 μg, or more of MUC-1 core repeat. One particular dosage of MUC-1 core repeat is in the range of about 500 μg to about 1500 μg, about 500 μg to about 1500 μg, and about 1000 μg.

Similarly, the amount of lipid A may be varied to match the amount of MUC-1 peptide formulated into the vaccine. Hence, the amount of lipid A may be about 50 μg, about 100 μg, about 200 μg, about 300 μg, about 400 μg, about 500 μg, about 600 μg, about 700 μg, about 800 μg, about 900 μg, about 1,000 μg, about 1,010 μg, about 1,020 μg, about 1,030 μg, about 1,040 μg, about 1,050 μg, about 1,060 μg, about 1,070 μg, about 1,080 μg, about 1,090 μg, about 1,100 μg, 1,200 μg, 1,300 μg, 1,400 μg, 1,500 μg, 1,600 μg, 1,700 μg, 1,800 μg, 1,900 μg, or about 2,000 μg, or more. In particular there may be about 500 μg of lipid A.

The BLP25 lipopeptide and lipid A may be associated with the lipid bilayer of the liposomes that are formed upon rehydration of the dry powder.

The formulation may be retained in a vial, such as in a 5 ml Type I borosilicate glass vial. The vial, which contains the MUC-1 formulation, also may contain other vaccine ingredients. For instance, the vial may comprise additional liposomal lipids, such as dipalmitoyl phosphatidiylcholine, cholesterol, and dimyristoyl phosphatidylglycerol. Each amount of those particular lipids may vary. Therefore, the amount of any one of dipalmitoyl phosphatidiylcholine, cholesterol, and dimyristoyl phosphatidylglycerol in a vial may be about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, or more than about 100 mg. The liposomal lipids may be contained in a second vial to the vial while the MUC-1 formulation may be contained in a first vial.

Other embodiments, of course, exist for the purposes of this invention. Hence, the above amounts of MUC-1 lipopeptide BLP25, adjuvant, and liposomal lipids in the L-BLP25 are given as examples only. Determining the appropriate amount of each constituent, including amounts of MUC-1 lipopeptide, can be readily accomplished. In some embodiments, the amount of MUC-1 lipopeptide will be greater or less than about 300 μg. The vaccine does not need to be supplied in a 5 ml Type I borosilicate glass vial, but may be supplied in any manner known in the art.

In one embodiment, the BLP25 lipopeptide is a linear 27-residue peptide that contains a lipidated amino acid derivative close to its C-terminus. Specifically, BLP25 comprises a palmitoyl lipid on a lysine residue at position 26 of the polypeptide. The sequence of the BLP25 lipopeptide is depicted in SEQ ID NO.: 2, shown below:

```
SEQ ID NO. 2:
STAPPAHGVTSAPDTRPAPGSTAPPK(palmitoyl)G
```

In other embodiments possessing a MUC-1 core sequence, an amino acid, such as threonine, serine, lysine, arginine, or cysteine, which may occur within the natural sequence of the peptide, may be a convenient site to which a lipid can be linked. In addition, the lipid can be linked to a synthetic amino acid or an amino acid not naturally found in the MUC-1 core sequence. Moreover, one or more of either the natural or synthetic amino acids can be added to either end or within the MUC-1 core sequence to facilitate the linking of a lipid.

The number of amino acids that can be added to the MUC-1 core sequence is not meant to be limiting, as any number of amino acids can be added as long as the peptide still functions in the methods of the invention. As demonstrated above, two additional amino acids have been added to the BLP25 polypeptide. That is, the C-terminus of the MUC-1 core sequence ends with a proline and is, therefore, 25-residues in length. In the case of the BLP25 polypeptide, however, a lysine and a glycine have been added to that C-terminal proline to facilitate the linkage of palmitoyl. Hence, the length of the BLP25 polypeptide is 27 amino acids long. Conventional peptide synthesis methods can be used to add one or more of such additional amino acids to a peptide sequence. Alternatively, the MUC-1 core sequence peptide or BLP25 can be made recombinantly.

In one particular embodiment, a BLP25 Liposome Vaccine ("L-BLP25") may comprise BLP25 lipopeptide, lipid A, cholesterol, DMPG, and DPPC. The BLP25 lipopeptide may comprise the sequence of SEQ ID NO: 2, an immunologically active fragment, or an immunologically active variant thereof. A dose of such a BLP25 Liposome Vaccine may comprise about 1000 μg of BLP25 lipopeptide, about 500 μg of lipid A, about 17.3 mg of cholesterol, about 3.6 mg of DMPG, and about 29.1 mg of DPPC.

This particular vaccine composition and dosage also can be described in "per vial" amounts. Hence, a vial may comprise about 300 μg of BLP25 lipopeptide, about 150 μg of lipid A, about 5.2 mg of cholesterol, about 1.1 mg of DMPG, and about 8.7 mg of DPPC.

This vaccine may be lyophilized and then reconstituted prior to administration, such as in sodium chloride solution. The BLP25 Liposome Vaccine quantities described above may be reconstituted, for example, in about 0.6 ml of liquid, although any volume of liquid, depending on the dosage desired, may be used, such as about 0.1 ml, 0.2 ml, 0.3 ml, 0.4 ml, 0.5 ml, 0.6 ml, 0.7 ml, 0.8 ml, 0.9 ml, 10 ml, 11 ml, 12 ml, 13 ml, 14 ml, 15 ml, 16 ml, 17 ml, 18 ml, 19 ml, or 20 ml, or more than 20 ml. The volume of liquid into which a lyophilized MUC-1 vaccine is reconstituted is not necessarily the volume that is administered to an individual.

A. MUC-1 Core Repeat Variants

As an alternative to the MUC-1 core repeat sequence depicted in SEQ ID NOs: 1 and 2, the formulation of the invention may incorporate immunologically active homologues or variants of those MUC-1 core repeats. Accordingly, the present invention encompasses the use of a MUC-1 core repeat peptide having a sequence that is similar to, but not identical to, the amino acid sequence depicted in either SEQ ID NO: 1 or SEQ ID NO: 2. Thus, the present invention contemplates the use of a MUC-1 core repeat that has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NO. 1 or SEQ ID NO: 2, and which is immunologically active.

A MUC-1 core repeat protein of the present invention may be modified to contain conservative variations or may be modified so as to change non-critical residues or residues in non-critical regions. Amino acids that are not critical can be identified by methods known in the art, such as site-directed mutagenesis, crystallization, nuclear magnetic resonance, photoaffinity labeling, or alanine-scanning mutagenesis (Cunningham et al., *Science,* 244:1081-1085 (1989); Smith et al., *J. Mol. Biol.,* 224:899-904 (1992); de Vos et al., *Science,* 255:306-312 (1992)). Modified proteins can be readily tested for activity or ability to induce an immune response via methods such as protease binding to substrate, cleavage, in vitro activity, or in vivo activity.

Specifically, a MUC-1 core repeat variant may incorporate 1, 2, 3, 4, or 5 amino acid substitutions that improve MUC-1 core repeat stability or with a different hydrophobic amino acid that improves MUC-1 core repeat stability against oxidation, or with a different amino acid that improves MUC-1 core repeat stability against protease. Thus, a "variant" MUC-1 core repeat polypeptide of the invention can differ in amino acid sequence from the sequence represented in SEQ ID NOs: 1 or 2 by one or more substitutions, deletions, insertions, inversions, truncations, or a combination thereof. Such a variant can be made to contain amino acid substitutions that substitute a given amino acid with another amino acid of similar characteristics. Conservative substitutions include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine. See Bowie et al., *Science,* 247:1306-1310 (1990).

B. MUC-1 Core Repeat Fusion Proteins

A MUC-1 core repeat peptide having the full-length sequence of SEQ ID NOs: 1 or 2, or a variant thereof, can also be joined to another polypeptide with which it is not normally associated. Thus, a MUC-1 core repeat peptide can be operatively linked, at either its N-terminus or C-terminus, to a heterologous polypeptide having an amino acid sequence not substantially homologous to the MUC-1 core repeat. "Operatively linked" indicates that the MUC-1 core repeat peptide and the heterologous polypeptide are both in-frame.

A fusion protein may, or may not, affect the ability of the MUC-1 core repeat, or a functional variant thereof, to induce an immunological reaction from a host system. For example, the fusion protein can be a Glutathione S-transferase (GST)-fusion protein in which MUC-1 core repeat is fused to the C-terminus of the GST sequence or an influenza HA marker. Other types of fusion proteins include, but are not limited to, enzymatic fusion proteins, for example, beta-galactosidase fusions, yeast two-hybrid GAL fusions, poly-His fusions, and Ig fusions. Such fusion proteins, particularly poly-His fusions, can facilitate the purification of recombinantly-produced MUC-1 core repeat for use in the invention. In certain host cells, expression and/or secretion of a protein can be increased by using a heterologous signal sequence fused to a protease that transports the MUC-1 core repeat peptide to an extracellular matrix or localizes the MUC-1 core repeat protein in the cell membrane.

Other fusion proteins may affect the ability of a MUC-1 core repeat to induce an immunological reaction. For example, a subregion of a MUC-1 core repeat can be replaced, for example, with the corresponding domain or subregion from another region of a MUC-1 protein. Accordingly, chimeric MUC-1 core repeats can be produced. Likewise, the affinity for substrate can be altered or even proteolysis of the substrate prevented. Accordingly, one may use a protein having a sequence of, for instance, SEQ ID NO: 1 or 2, or variant thereof, as a competitive inhibitor of another MUC-1 core repeat peptide.

C. MUC-1 Core Repeat Modifications

MUC-1 core repeat variants also encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the MUC-1 polypeptide, such as a leader or secretory sequence or a sequence for purification of the polypeptide.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Particularly common peptide modifications that can be applied to MUC-1 core repeat include glycosylation, lipid attachment, sulfation, gamma-carboxylation of glutamic acid residues, hydroxylation, and ADP-ribosylation. See T. E. Creighton, *Proteins-Structure and Molecular Properties,* 2nd Ed. (W. H. Freeman and Company, New York (1993)); Wold, F., *Posttranslational Covalent Modification of Proteins*, B. C. Johnson, Ed. (Academic Press, New York 1-12 (1983)); Seifter et al., *Meth. Enzymol.,* 182: 626-646 (1990); and Rattan et al., *Ann. N.Y. Acad. Sci.,* 663:48-62 (1992).

Modifications can be made anywhere in a MUC-1 core repeat polypeptide, including the peptide backbone, the amino acid side-chains, and the amino or carboxyl termini. Blockage of the amino or carboxyl group in a polypeptide, or both, by a covalent modification, is common in naturally-occurring and synthetic polypeptides.

II. BLP25 Dosages

When a MUC-1-based formulation, including a MUC-1 core peptide, BLP25 polypeptide, or BLP25 liposomal vaccine is being given to a subject, one of skill in the art understands that the dosage may depend on several factors, including, but not limited to, the subject's weight, tumor size, or tumor progression. Generally, as used herein, a subject that receives the MUC-1-based formulation is a single organism. In certain embodiments, a subject will be a mammal. Specifically, a subject may be human, including being a male or a female. In many embodiments, the subject will be a patient, or an individual awaiting or under medical care and treatment.

A subject may be given a dose of about 50 μg, about 100 μg, about 200 μg, about 300 μg, about 400 μg, about 500 μg, about 600 μg, about 700 μg, about 800 μg, about 900 μg, about 1,000 μg, about 1,010 μg, about 1,020 μg, about 1,030 μg, about 1,040 μg, about 1,050 μg, about 1,060 μg, about 1,070 μg, about 1,080 μg, about 1,090 μg, about 1,100 μg, 1,200 μg, 1,300 μg, 1,400 μg, 1,500 μg, 1,600 μg, 1,700 μg, 1,800 μg, 1,900 μg, or about 2,000 μg of BLP25 MUC-1 polypeptide that is in the BLP25 liposome vaccine, in either single or cumulative applications. In specific embodiments, the dose given to the subject is about 1,000 μs of the MUC-1-based formulation per week.

A subject may receive a dose of the MUC-1-based formulation, for example, multiple times daily, every day, every other day, once a week, or any other suitable dosing regimen. In one embodiment, routinely administering encompasses administering a dose of BLP25 liposome vaccine once a week for a period of time. Of course, the dosing regimen may comprise other permutations of MUC-1 peptide delivery. That is, the vaccine may be administered once, twice, three times, four times, five times, six times, or more times a week. In some embodiments, subjects will be given at least 5 doses over a period of time. In other embodiments, subjects will be given greater than or fewer than 5 doses. Thus, a subject may receive a dose of about 1,000 μg of the MUC-1 lipidated polypeptide every week. Alternatively, the subject may receive two doses of 500 μg, twice a week, or a daily 100 μg dose over five days.

These dosage examples are not limiting and only used to exemplify particular dosing regimens for administering about 1,000 μg of the MUC-1 lipidated polypeptide. For instance, if the appropriate dose for a given situation is 1,000 μg per week, the doses may be broken down into any number of permutations. This also holds true if the appropriate dose for a particular situation is greater than or less than 1,000 μg.

The period of time that the MUC-1-based formulation is administered to the subject may be any suitable period.

Examples of such suitable periods include, but are not limited to, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, or at least about 24 months or longer. The treatment period also may continue for longer than 24 months, if desired, such as for 30 months, 31 months, 32 months, 33 months, 34 months, 35 months, 36 months, or longer than 36 months.

In another embodiment of the invention, the period of time of dosing for any of the methods described herein is for at least about 2 weeks, at least about 4 weeks, at least about 8 weeks, at least about 16 weeks, at least about 17 weeks, at least about 18 weeks, at least about 19 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, at least about 60 weeks, at least about 68 weeks, at least about 72 weeks, at least about 80 weeks, at least about 88 weeks, at least about 96 weeks, or at least about 104 weeks.

The MUC-1-based formulation may be administered in different phases of treatment. For example, the MUC-1-based formulation may be administered in both a treatment phase and a maintenance phase. In some embodiments, the treatment phase will comprise administration of the MUC-1-based formulation in weekly dosages, whereas the maintenance phase may be in longer time periods, such as about every 6 weeks, about every 7 weeks, about every 8 weeks, about every 9 weeks, about every 10 weeks, about every 11 weeks, about every 12 weeks, or longer. In some cases, the dosage given in the treatment phase will be greater than the dosage given in the maintenance phase. However, treatment and maintenance phases may be designed to a particular individual so the time and dosages between the treatment and maintenance phases may significantly vary from the above examples. Generally, the maintenance phase may begin at any time deemed appropriate. For example, in some embodiments, the treatment phase will be eight weeks and the maintenance phase will continue throughout the individual's lifetime. In other embodiments, only a treatment or a maintenance phase will be undertaken.

In yet further embodiments, the MUC-1-based formulation will be given prophylacticly. In these embodiments, the administration of the MUC-1-based formulation may prevent an individual from developing cancer, such as NSCLC or prostate cancer. When the MUC-1-based formulation is used prophylacticly, the dosage amount and regime can be readily determined.

Physicians can determine the amount of time that a subject should remain on the MUC-1-based formulation. In some cases, it may be advantageous to administer the MUC-1-based formulation for the rest of an individual's lifetime.

III. Liposomes

In many embodiments, the MUC-1-based formulation will be used with liposomes. Liposomes are microscopic vesicles that consist of one or more lipid bilayers surrounding aqueous compartments. See e.g., Bakker-Woudenberg et al., *Eur. J. Clin. Microbiol. Infect. Dis.* 12 (Suppl. 1): S61 (1993), and Kim, *Drugs,* 46: 618 (1993). Because liposomes can be formulated with bulk lipid molecules that are also found in natural cellular membranes, liposomes generally can be administered safely and are biodegradable. Thus, liposomes are often used in drug delivery.

Depending on the method of preparation, liposomes may be unilamellar or multilamellar, and can vary in size with diameters ranging from about 0.02 μm to greater than about 10 μm. A variety of agents can be encapsulated in or inserted into liposomes. Hydrophobic agents partition in the bilayers and hydrophilic agents partition within the inner aqueous space(s). See e.g., Machy et al., Liposomes in Cell Biology and Pharmacology (John Libbey, 1987), and Ostro et al., *American J. Hosp. Pharm.* 46: 1576 (1989).

Liposomes can adsorb to virtually any type of cell and then release an incorporated agent. In some cases, the liposome can fuse with the target cell, whereby the contents of the liposome then empties into the target cell. Alternatively, a liposome may be endocytosed by cells that are phagocytic. Endocytosis is followed by intralysosomal degradation of liposomal lipids and release of the encapsulated agents. Scherphof et al., *Ann. N.Y. Acad. Sci.,* 446: 368 (1985).

Additionally, liposomes can be used to present active agents, such as polypeptides, at their surface and, therefore, induce various events, such as signaling cascades or initiate biochemical pathways, without fusing to a target cell or surface as mentioned in the preceding paragraph. Thus, for example, a polypeptide may be incorporated into the lipid bilayer, for instance, of a liposome via a lipid that is attached to the polypeptide.

Liposomes are used as delivery vehicles with the MUC-1-based formulations of the present invention. Exemplary suitable liposomes that may be used in the methods of the invention include multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). However, as understood by one having skill in the art, the type of liposome is not meant to be limiting and may include any liposome made in any matter that is compatible with the methods of the invention. Techniques for preparing liposomes are well known in the art. See Colloidal Drug Delivery Systems, vol. 66 (J. Kreuter ed., Marcel Dekker, Inc. (1994)).

IV. Lipids

In many embodiments, the MUC-1-based formulation may be lipidated, such as with SEQ ID NO.: 2. As used herein, a "lipid" may be a myristyl, palmitoyl, or a lauryl molecule that can be attached to amino acids that possess functional oxygen, nitrogen, or sulfur groups. Such amino acids include, but are not limited to, threonine, serine, lysine, arginine, and cysteine.

A "monolipopeptide" is a peptide to which only one lipid chain is attached. Similarly, a "dilipopeptide" is a peptide that has two lipid chains attached to either one or two amino acids. If the two lipid chains are attached to two amino acid residues, those residues can be spaced any number of amino acids apart. In cases where more than one lipid is attached, the lipids may either be the same lipid or may be different lipids. Similarly, if more than two lipids are attached, two or more of the lipids may be the same or all of the lipids may be dissimilar.

It is believed that a lipopeptide, such as BLP25, can be incorporated into a liposome because the lipid portion of that peptide spontaneously integrates into the lipid bilayer of the liposome. Thus, in this case, a lipopeptide may be presented on the "surface" of a liposome. Alternatively, a peptide may be encapsulated within a liposome. Techniques for preparing and formulating liposomes with molecules such as peptides are well known.

V. Exemplary Adjuvants

The present MUC-1-based formulation may also include one or more adjuvants. Alternatively, one or more adjuvants may be administered either before, in conjunction with, or after administration of the MUC-1-based formulation of the invention.

As is well appreciated, adjuvants are substances that act in conjunction with specific antigenic stimuli to enhance a specific response to an antigen. Monophosphoryl lipid A (MPLA), for example, is an effective adjuvant that causes increased presentation of liposomal antigen to specific T Lymphocytes. Alving, C. R., *Immunobiol.,* 187:430-446 (1993). MPLA may bind to toll-like receptors, which can lead to activation of defense signaling pathways that control the expression of various immune response genes.

Lipid-based adjuvants, such as Lipid A and derivatives thereof, are suitable for use with the MUC-1-based formulations. When incorporated into liposomes, a muramyl dipeptide (MDP) has also been shown to increase adjuvancity (Gupta R K et al., Adjuvants-A balance between toxicity and adjuvancity," *Vaccine,* 11, 293-306 (1993)).

Another class of adjuvants that may be used with the present invention includes stimulatory cytokines, such as interleukin-2 (IL-2). Thus, the present liposomal vaccines may be formulated with IL-2, or IL-2 may be administered separately for optimal antigenic response. In many embodiments, IL-2 is beneficially formulated with liposomes.

Synthetic mimics of adjuvants also may be co-formulated with use of the MUC-1-based formulations. For example, a lipid A mimic may be used in conjunction with the liposomal vaccine. One particular type of lipid A mimic is one in which one or both of the sugar units of the lipid A disaccharide is replaced with at least the carbon skeleton of pentaerythritol. See, for instance, WO 03/094850, which is incorporated herein by reference.

VI. Exemplary Vaccine Formulations

When the MUC-1-based formulation is a vaccine, the vaccines may also be formulated with one or more pharmaceutically acceptable excipients. The properties of such excipients are well known in the art, but typically include excipients that are physiologically tolerable and inert or enhancing with respect to the vaccine properties of the inventive compositions. Non-limiting examples of pharmaceutically acceptable excipients include liquid vehicles such as sterile, physiological saline. An excipient may be added at any point in formulating a liposomal vaccine or it may be admixed with the complete vaccine composition. One can easily determine both when to add the excipient and the appropriate excipient for use with the vaccines of the invention.

One particular vaccine formulation may comprise about 300 μg of MUC-1 lipopeptide BLP25 of SEQ ID NO: 2, about 150 μg of lipid A, and about 15 mg of one or more additional liposomal lipids, such as dipalmitoyl phosphatidiylcholine, cholesterol (DPMC), and dimyristoyl phosphatidylglycerol (DPMG).

VII. Cyclophosphamide

Prior to treatment with a MUC-1-based formulation, a subject may be "pretreated" with cyclophosphamide. In many embodiments, the dose of cyclophosphamide will be about 300 mg/m$^2$, about 400 mg/m$^2$, about 500 mg/m$^2$, or about 600 mg/m$^2$. A dose of cyclophosphamide in the range of about 300 mg/m$^2$ is considered a low dose. In certain embodiments, the cyclophosphamide will be given in a single dose. In other embodiments, the cyclophosphamide will be given in more than one dose over a period of time.

The use of a dose cyclophosphamide, such as 300 mg/m$^2$, may partly overcome the immune suppression seen in some cancer patients. In various animal models, cyclophosphamide has been shown in certain subjects to augment delayed-type hypersensitivity responses, increase antibody production, abrogate tolerance, and potentiate antitumor immunity. Other drugs that affect the immune system in a similar manner to cyclophosphamide may also be used in pretreatment regimens with the formulations of the present invention.

VIII. Route of L-BLP25 Vaccine Administration and Targeting

The MUC-1-based formulations of the invention, including the vaccines, may be formulated for multiple routes of administration. Specific routes include any pharmaceutically suitable method of administration, such as via intravenous, intramuscular, subcutaneous, or intradermal injection, aerosol, transdermal, pulmonary, nasal, oral, vaginal, rectal, ocular, local (powders, ointments or drops), buccal, intracisternal, intraperitoneal, or topical administration, and the like, or by a combination of these routes, administered at one time or in a plurality of unit dosages. The vaccine or the liposomally-bound MUC-1 core repeat peptide also may be administered via a formulation suitable for transdermal delivery, such as via a transdermal patch.

Administration of vaccines is well known and ultimately depends upon the particular formulation and the judgment of the attending physician. MUC-1 based formulations, such as L-BLP25 can be maintained as a suspension or they may be lyophilized and hydrated later to generate a useable formulation.

In some embodiments, such as the embodiment in example 1, one dose of MUC-1-based formulation may be injected into several different sites. For example, in the embodiment of example 1, 1,000 μg of MUC-1-based polypeptide may be given in four sub-doses of approximately 250 μg each. In the case of injections, the amount of the injection is irrelevant as long as the appropriate dose or sub-dose of inventive composition is being given. For example, one injection may be 1 cc (ml), while another injection with the exact same dose may be 5 cc (ml). Furthermore, the amount in the sub-dose is meant as a non-limiting example only and embodiments where the sub-doses are more or less than ¼ of the full dose are anticipated.

The sub-dose or doses may be administered in the deltoid or triceps region of the upper arms, and the left and right anterolateral aspects of the abdomen. However, these injection sites are meant as examples only. In some embodiments, only two sub-doses will be given and these sub-doses may be given in any of the regions set forth above. In yet further embodiments, sub-doses or complete doses will be given in completely different regions. If the MUC-1-based formulation is injected, then an appropriate injection site can be easily determined.

To provide greater specificity, thus theoretically reducing the risk of toxic or other unwanted effects during in vivo administration, in some embodiments inventive compositions will be targeted to the cells through which they are designed to act, namely antigen-presenting cells. This may conveniently be accomplished using conventional targeting technology to direct a liposome containing an immunogenic peptide to a particular location within the body. To target antigen presenting cells, for example, mannose and the Fc portion of antibodies can be chemically conjugated to an antigenic peptide, or the targeting peptide may be recombinantly fused to the immunogenic lipopeptide. Other, similar strategies will be familiar to the practitioner. Nonetheless, in some embodiments the inventive compositions will not be targeted to specific cell types or organs.

IX. Individuals for Treatment

Any subject diagnosed with a cancer susceptible to treatment with a MUC-1-based formulation, such as NSCLC and prostate cancer, may receive treatment with the MUC-1-based formulations described herein. Alternatively, any individual who exhibits symptoms of any stage of a cancer susceptible to treatment with a MUC-1-based formulation, such as symptoms of any stage NSCLC or any stage of prostate cancer, but who has not been formally diagnosed as having the cancer, may also receive treatment with the MUC-1-based formulations. Furthermore, as stated above, the MUC-1-based formulations may be given prophylacticly to prevent a subject from contracting a cancer susceptible to treatment with a MUC-1-based formulation, such as NSCLC or prostate cancer.

In selecting a subject with a cancer susceptible to treatment with a MUC-1-based formulation, such as a subject with NSCLC and/or prostate cancer, for treatment with the MUC-1-based formulation, it may be beneficial to determine the level of MUC-1 in the subject's serum either before or during treatment. In certain cancer patients, high serum MUC-1 levels have been correlated with poor prognosis. See, for instance, Pihl et al., *Pathology,* 12:439-447 (1980). Because an abnormal amount of circulating MUC-1 may inhibit or reduce the effectiveness of the interactions of exogenous MUC-1-based formulations, knowing the amount of endogenous MUC-1 may assist in deciding the appropriate dose of MUC-1-based formulations to be administered to a subject.

A. Tumor Marker CA27.29 (MUC1)

CA27.29 is the name for an antigen that is a particularly useful target for identifying MUC-1 protein, especially for identifying MUC-1 protein fragments circulating in a subject's bloodstream, or in a suitable biological sample, such as in a blood, urine, or serum sample.

The CA27.29 antigen can be detected by a monoclonal antibody that is specific for the protein core of the MUC1 product. Minimum epitope mapping with overlapping synthetic peptides can be used to identify a suitable monoclonal antibody. One such antibody is B27.29.

Several variables, such as the number of MUC-1 tandem repeats and the posttranscriptional glycosylation of MUC-1 epitopes, can affect in vivo detection and quantification of MUC1-related markers. In vivo detection of MUC-1 and its fragments may be further complicated by the presence of circulating anti-mucin autoantibodies, occasionally found in cancer patients as a result of a host response to altered mucin biochemistry. These antibodies are capable of forming mucin-antibody mucin immunocomplexes which may affect MUC1 detection, depending on the assay format. See Gion et al., *Clinical Chemistry,* 45: 630-637 (1999), which is incorporated herein by reference.

Any method can be used to detect or assay for amounts of CA27.29 antigen in a subject's blood sample, such as an enzyme-linked immunosorbent assay. Another assay is the ACS:180 BR assay (Bayer Diagnostics), which is a fully automated competitive chemiluminescent immunoassay. A mouse monoclonal antibody, raised against a peptide epitope in the tandem region of the MUC-1 backbone and labeled with acridinium ester, is incubated for 7.5 min with both the patient sample and purified CA27.29 coupled covalently to paramagnetic particles (solid phase). Both the antigen in the sample and the solid-phase CA27.29 compete for binding to the labeled antibody. Therefore, an inverse relationship is found between the amount of antigen in the sample and the amount of relative light units detected by the system. The assay can be performed according to the instructions of the manufacturer.

Another assay is the TRUQUANT BR radioimmunoassay, which uses monoclonal antibody B27.29 noted above to quantitate CA27.29 mucin antigen in serum. See MacLean et al., *J. Immunother.,* 20(1):70-8 (1997).

Typically, in the present case exemplified in Example 4, a normal level of CA27.29 antigen in serum or circulating blood is about 37.7 U/ml. Levels of serum MUC-1 that are greater than about 37.7 U/ml indicates an abnormal.

It is well within the purview of the skilled person to determine threshold levels of circulating MUC-1 peptides, such as the CA27.29 antigen, in different groups of individuals. That is, the value "37.7 U/ml" is not necessarily a definitive threshold for all assayable populations. A "normal" quantity of circulating CA27.29, for instance, can be determined from a desired subpopulation and used as an indicator to classify C27.29 quantities as either normal or abnormal.

In the present case, the upper limit for normal levels of circulating MUC-1, as measured by C27.29 levels, was 37.7 U/ml. According to the present invention, therefore, an individual with a MUC-1 level that is about 37.7 U/ml or lower than about 37.7 U/ml is a suitable candidate for treatment with a MUC-1 based vaccine, such as with BLP25, or one of the other MUC-1 formulations described herein.

Also according to the present invention, a subject with a MUC-1 level that is at or lower than a different "threshold" normal level of circulating MUC-1 is also a suitable candidate for treatment with a MUC-1 based vaccine, such as with BLP25, or one of the other MUC-1 formulations described herein.

B. HLA A2 Typing

The term HLA refers to the Human Leucocyte Antigen System, which is controlled by genes on the short arm of chromosome six. The HLA loci are part of the genetic region known as the Major Histocompatibility Complex (MHC). The MHC has genes (including HLA) which are integral to normal function of the immune response. The essential role of the HLA antigens lies in the control of self-recognition and thus defence against microorganisms. Some HLA antigens are recognised on all of the tissues of the body, rather than just blood cells.

Human leucocyte antigen (HLA) A2 is the most heterogeneous allele at the HLA A locus, with approximately 56 different subtypes. Substantial heterogeneity in A02 distribution has been observed in populations worldwide. HLA B40 is the most common allele associated with A2 haplotypes. HLA A2 has also been implicated in a number of diseases including Alzheimer's, psoriatic arthritis, vitiligo, and pulmonary tuberculosis.

It is possible to detect the presence of either the HLA A2 protein in an individual's blood or tissue sample or of DNA or RNA. Hence, in the latter kind of assay, the polymerase chain reaction (PCR) can be employed to detect HLA A2 DNA, RNA, or cDNA. For instance, PCR-based reverse blot sequence-specific oligonucleotide hybridisation technique. Alternatively Southern or Northern blots with an HLA A2-specific probe may be employed. On the other hand, an antibody can be used to detect HLA A2 protein.

The presence or absence of HLA nucleic acid or the HLA A2 protein is a factor to be considered in preparing the subject for treatment with a MUC-1 based vaccine, such as with BLP25.

X. Individuals with NSCLC

When subjects with NSCLC are to be treated with a MUC-1-based formulation of the invention, subjects diagnosed as having stage IIIB locoregional (LR), stage IIIB with malignant pleural effusion, or stage IV NSCLC specifically may be treated. Nevertheless, the present invention also encompasses the treatment of NSCLC individuals other than those having stage III locoregional, stage III pleural effusion, and stage IV disease. Thus, the present invention contemplates treatment of stage IA, stage IB, stage IIA, stage IIB, stage IIIA, stage IIIB, stage IIIB locoregional, stage IIIB pleural effusion, and stage IV NSCLC-diagnosed patients. See Mountain C. F., *Chest,* 111(6):1710-7 (1997), which is incorporated herein by reference.

A. Lung Cancer Staging

Generally, when the MUC-1-based formulations are used in subjects with NSCLC, the stage of NSCLC in the individual may be determined before, after, or during treatment. An outline of lung cancer staging is set forth below:

Normally in lung cancer, an increasing "stage" number correlates with a worse prognosis. To diagnose an individual at a particular stage, the size and the location of the primary tumor ("T" value), as well as the degree of nodal involvement and increasing probability of metastases ("N" value), are taken into consideration. Also noted when diagnosing individuals is the absence ("M0") or presence ("M1") of metastases.

1. T Category

The T category is made up of subcategories, T1-T4, whereby an increasing number from 1 to 4 represents increasing size and local invasion by the primary tumor. T1 and T2 are differentiated primarily on size, for example, T1 is less than 3 cm while T2 is larger than 3 cm. T3 tumors typically involve the chest wall, and include but are not limited to, the superior pulmonary sulcus, diaphragm, mediastinal pleura, pericardium, or proximal main stem bronchus, but may be resectable. T4 tumors are not surgically resectable because they may have invaded the mediastinum and may involve the heart, great vessels, trachea, carina, or esophagus, or in the case of a malignant pleural effusion, the pleura.

2. N Category

Nodal stages are divided into N1, N2, and N3. N1 nodes typically involve peribronchial or ipsilateral hilar nodes. These nodes are intrapleural in position. N2 nodes typically involve ipsilateral mediastinal or subcarinal nodes. N3 nodes typically involve contralateral hilar, or mediastinal, any scalene nodes, or supraclavicular nodes.

3. NSCLC Stages

The "stages" of NSCLC, therefore, represent distinct classifications of NSCLC that are based on the various permutations of T, N, and M values. The recognized stages of NSCLC are as follows:

Occult Carcinoma:

In this category, patients are classified as TX N0 M0, meaning that they have had malignant cells detected in their bronchopulmonary secretions, but there is no tumor evident by bronchoscopic or radiographic methods.

Stage IA and Stage IB:

Stage IA is classified as T1 N0 M0 based upon a significantly better 5 year survival outcome than patients with stage IB disease (T2 N0 M0). Surgery is the preferred treatment for these patients. In 1997, the 5 year survival rate for patients surgically staged as stage IA was 67% and for stage IB was 57%.

Stage IIA and Stage IIB:

Stage IIA disease is defined as T1 N1 M0 and has a 55% survival rate at 5 years based on surgical staging. Stage IIB disease is composed of T2 N1 M0 and T3 N0 M0. The designation of T3 N0 M0 represents extrapulmonary extension of the tumor without lymph node involvement. The classification T3 N0 M0 is grouped with T2 N1 M0 because their respective 5 year survival rates for surgically staged disease, 38% versus 39%, are not significantly different. Surgery is also the primary treatment for these individuals.

Stage IIIA:

Stage IIIA patients are considered to be resectable, while Stage IIIB patients are not. Stage IIIA patients are defined by lesions with extrapulmonary extension (T3) and limited lymph node involvement (N1 or N2). The nodal involvement may extend to the ipsilateral mediastinal, and/or subcarinal lymph nodes. These patients are classified as either T3 N1 M0, or T1-3 N2 M0. As of 1997, the 5 year survival rate for stage IIIA disease was 23%.

Stage IIIB:

Stage IIIB classification refers to patients who have extrapulmonary involvement including, but not limited to contralateral mediastinal or hilar lymph nodes; ipsilateral or contralateral supraclavicular or scalene nodes; extensive mediastinal nodes without distant metastases; or cytology positive malignant pleural effusion. These patients can be classified as either T1-3 N3 M0 or T4 N0-3 M0. In 1997, the 5 year survival rate for clinically staged disease was 5% with multimodal therapy.

Stage IV:

Stage IV is defined by any metastatic involvement. These patients are classified as M1 with any T and any N. As of 1997, more than a quarter of patients with NSCLC had clinical stage IV.

XI. Individuals with Prostate Cancer

Similar to the low survival rate of individuals with advanced stage lung cancer who under go multimodal therapy, men with prostate cancer who experience biochemical failure after a prostatectomy have few therapeutic options. One therapeutic option they do have is androgen deprivation therapy (ADT). Unfortunately, this therapy has significant morbidity, especially if used for long periods of time.

In individuals with prostate cancer, it is known, for instance, that prostate-specific antigen ("PSA") levels in the blood tend to rise when the prostate gland enlarges. Accordingly, PSA is a good biological or tumor marker for prostate cancer. In individuals with more advanced disease, treatment-induced decline in PSA correlates with improved survival (Scher et al., *J. Natl. Cancer Inst.,* 91(3):244-51 (1999)).

XII. Treatment of Individuals with NSCLC or Prostate Cancer

The present invention encompasses treatment with the MUC-1-based formulations of the invention of NSCLC individuals in all NSCLC stages as well as the treatment of individuals with prostate cancer, including individuals with prostate cancer that have PSA failure, post radical prostatectomy. The use of the phrase "treating" is meant that the formulation or vaccine is useful for preventing, curing, reversing, attenuating, alleviating, minimizing, suppressing, or halting the deleterious effects of a disease state, disease progression, disease causative agent, or other abnormal condition.

In some embodiments, individuals with either NSCLC or prostate cancer may have been previously treated with radiation or surgery, prior to treatment with the inventive compositions. Individuals may also undergo treatment with chemotherapy, radiation, or surgery before, while, or after they have been treated with the MUC-1-based formulations of the invention. In the case of these individuals, any accepted cancer treatment may be given before, during, or after treatment with the MUC-1-based formulations.

When choosing individuals to treat with the formulations and vaccines of the present invention, inclusion and exclusion criteria may be used. For example, in one embodiment, when NSCLC individuals are to be treated with the MUC-1-based formulation, individuals to be treated may be men or women over the age of 18 whose disease is stable or who have responded to treatment following completion of their first line standard chemotheraphy. Individuals other than those above may be treated with the MUC-1-based formulations. In fact, some individuals treated with the inventive compositions will not have been treated with chemotheraphy prior to treatment with the MUC-1-based formulation.

XIII. Possible Inclusion and Exclusion Criteria for Individuals with NSCLC

In another embodiment, an individual with NSCLC chosen for treatment has an Eastern Cooperative Oncology Group (ECOG) performance status of ≤2, with a neturophil count≥$1.5\times10^9$/L; platelet count≥$100\times10^9$/L; WBC≥$2.5\times10^9$/L and hemoglobin 90 g/L. Although the ECOG numbers may be used to evaluate individuals for treatment, particular ECOG numbers are not required before, during, or after treatment.

Other inclusion criteria may include an expected survival of four months and where the individual has understood and signed a written consent. Of course, these are not set inclusion criteria and treatment of individuals with lower life expectancies are envisioned. Furthermore, as MUC-1-based formulation become mainstream cancer treatments, individuals will likely have the inventive compositions prescribed and no signed written consent will be required.

Regarding individuals with NSCLC who may be excluded from treatment, the exclusion criteria are meant as guidelines only. In many cases, individuals exhibiting one or more of the exclusion criteria, including all of the exclusion criteria, may still be treated with the MUC-1-based formulations. Examples of exclusion criteria for NSCLC individuals include: (a) surgery or immunotherapy within four weeks prior to treatment, (b) immunosuppressive drugs including systemic cortiocosteriods within three weeks prior to treatment, (c) past or current history of neoplasm other than lung carcinoma, (d) autoimmune disease or recognized immunodeficiency disease, (e) clinically significant hepatic or renal dysfunction, (f) significant cardiac disease or active infection, or (g) individuals who had had a splenectomy.

XIV. Possible Inclusion and Exclusion Criteria for Individuals with Prostate Cancer Similar to individuals with NSCLC, individuals with prostate cancer may also be subjected to inclusion and exclusion criteria. Once again, these criteria are guidelines only and an individual with prostate cancer who does not satisfy any of the inclusion criteria or satisfies any of, or all of, the exclusion criteria may still be treated under the methods of the present invention. For individuals with prostate cancer, inclusion criteria may include: (a) radical prostatectomy at least 6 months before treatment, (b) three consecutive increased serum PSA values post-radical prostatectomy with at least a 50% increase above the post-prostatectomy nadir, (c) no evidence of malignant disease at pre-treatment evaluations as evidenced by negative pelvic CT and bone scan, (d) ECOG performance status of 0, 1, (e) normal haematological, hepatic and renal function tests, (f) understand and sign a written informed consent; and (g) individuals who have ever been treated with hormonal therapy for prostate cancer (i.e., neoadjuvant treatment pre-RP) must have serum testosterone within the normal range. As stated above, these inclusion criteria are only guidelines and many individuals with different criteria may be treated using the methods of the invention. For example, individuals with prostate cancer who have not had a radical prostatectomy may be treated. Furthermore, individuals who do not have increased serum PSA or whose serum PSA has not increased either consecutively or is not above 50% as compared to the post-prostatectomy nadir may also be treated.

Exclusion criteria that may be used, although not required, for individuals with prostate cancer include: (a) hormonal therapy within 6 months prior to treatment, (b) immunotherapy within 4 weeks prior to treatment, (c) radiotherapy to the prostate bed within one year prior to treatment, (d) treatment with immunosuppressive drugs such as cyclosporin or adrenocorticotropic hormone (ACTH) or requiring chronic treatment with corticosteroids, (e) known autoimmune or immunodeficiency disease, or (f) clinically significant cardiac disease or active infection. Once again, these exclusion criteria are examples only. For example, individuals with both prostate cancer and clinically significant cardiac disease may be treated with the methods of the present invention in individual cases.

XV. Effects of Treatment

Treatment with the MUC-1-based formulations described herein may result in various effects. One effect of treating a NSCLC-diagnosed individual, specifically a stage IIIB NSCLC-diagnosed individual, with the MUC-1-based formulation is an increase in the length of survival. Similarly, administering the described MUC-1-based formulation an individual may impact that individual's "quality of life" or "health-related quality of life." An increase in survival, as well as an impact on quality of life, may also be seen in treated individuals with prostate cancer. Moreover, in certain individuals with prostate cancer, treatment with the MUC-1-based formulation will result in lower PSA, stabilized PSA, or decreased PSA doubling rates.

Comparisons of the effects of treatment with MUC-1-based formulations can be made between treated individuals and individuals who are either undergoing no care or individuals who are undergoing best supportive care (BSC). BSC comprises many alternative types of care that do not include treatment with the MUC-1-based formulation. For example, BSC, although usually discretionary depending on the circumstances, may include psychosocial support, analgesics, and nutritional support. In some embodiments, comparison of the effects of treatment will be made between individuals receiving differing amounts of the MUC-1-based formulation. In yet further embodiments, individuals will undergo BSC in conjunction with treatment with the MUC-1-based formulations.

Before treatment of an individual with the MUC-1-based formulations of the present invention, individuals may undergo pre-treatment evaluation. A non-limiting example of a pre-treatment evaluation includes a complete history and physical examination. The physical examination may include such things as a CT scan or X-ray. Individuals may also undergo treatment evaluations during the course of treatment. A treatment evaluation may include monitoring the individual's vital signs, inspecting injection sites, and analyzing blood samples.

A treated individual may also be evaluated by determining the: (a) tumor size, (b) tumor location, (c) nodal stage, (d)

growth rate of the NSCLC or prostate cancer, (e) survival rate of the individual, (f) changes in the individual's lung cancer or prostate cancer symptoms, (g) changes in the individual's PSA concentration, (h) changes in the individual's PSA concentration doubling rate, or (i) changes in the individual's quality of life.

XVI. Increased Survival Time in NSCLC Individuals by Administering MUC-1-Based Formulation or BLP25 Liposome Vaccine One of the advantages to treating an individual with NSCLC or prostate cancer with the MUC-1-based formulations of the invention is that the individual may have a longer survival time than an individual who does not receive treatment with the inventive compositions. Survival rates may be determined by comparing the current number of survivors with the number of individuals who started treatment with the MUC-1-based formulation. In other embodiments, survival rates may be compared to published survival rates for a particular type of cancer. In general, the survival rate may be measured at any time following the start of treatment.

For example, the survival rate may be measured at less than 6 months following the start of treatment, greater than 6 months but less than a year, a year or greater but less than 2 years, 2 years or greater but less than 5 years, or 5 or greater years. In some embodiments, an increased survival rate will be evidence that the MUC-1-based formulations of the invention are effecting a particular individual.

XVII. Maintaining the Quality of Life and Lung Cancer Symptoms by Administering MUC-1-Based Formulations As set forth above, another advantage of treating an individual with NSCLC or prostate cancer with the MUC-1-based formulations of the invention is maintenance or an increase in the individual's quality of life. Clinicians and regulatory agencies recognize that an individual's "quality of life" ("QoL") is an important endpoint in cancer clinical trials. See, for instance, Plunkett et al., Clin. Lung Cancer, 5(1):28-32 (2003), and Cella et al., J. Clin. Epidemiol., 55(3): 285-95 (2002), which are each incorporated herein by reference.

Four of the most important quality of life indicators are physical and occupational function, psychologic state, social interaction, and somatic sensations. In this respect, in individuals with NSCLC, two lung cancer questionnaires, the European Organization for Research and Treatment of Cancer ("EORTC") and the Functional Assessment of Cancer Therapy ("FACT-L"), can be used to assess an individual's, specifically an individual's, health-related quality of life before, during, and after treatment with the MUC-1-based formulations described herein.

It is anticipated that the methods of the invention may be used in conjunction with assessments according to various subscales that monitor an individual's Physical Well-being (PWB), Social/Family Well-being (SWB), Emotional Well-being (EWB), Functional Well-being (FWB), and Lung Cancer Symptom subscale (LCS). Although the Lung Cancer Symptom subscale is obviously tailored to individuals with lung cancer, different subscales may be used with different types of cancer. Thus, a different subscale may be used with individuals with prostate cancer. Depending on which "Well-being" scores are combined, one may obtain a "FACT-L score" (the sum of all of the subscales) or a "Trial Outcome Score (TOI)" (the sum of the PWB, FWB, and LCS subscales). The TOI is a reliable indicator of meaningful change in quality of life. See, Cella et al., supra.

The individual may be assessed for their FACT-L and TOI scores before, during, and after treatment with the MUC-1-based formulations of the invention. For instance, the TOI score may be taken at baseline, i.e., pre-treatment, and then at various intervals after treatment has started, i.e., at 4 weeks, 8 weeks, 19 weeks, 31 weeks, or 43 weeks, or longer. These various intervals are examples only and the quality of life indicators may be taken at any appropriate time. For example, the first TOI score may be taken after the first treatment, instead of at a baseline. Then, the change in scores between various time points may be calculated to determine trends relating to improving, worsening, or maintaining of quality of life.

It has been calculated that a decrease of 3 points or more from baseline for LCS is a clinically meaningful worsening in lung cancer symptoms and an increase in 3 or more points is a clinically meaningful improvement in lung cancer symptoms. Likewise for TOI scores, a decrease of 7 or more points indicates a worsening in quality of life, while an increase of 7 or more points indicates an improvement in quality of life.

In some embodiments, a clinical improvement in lung cancer symptoms or quality of life will demonstrate that the MUC-1-based formulations are effecting the particular individual.

Thus, administering the MUC-1-based formulations of the invention may be useful in improving or maintaining the quality of life of treated individuals that have NSCLC or prostate cancer. In measuring the effect on the quality of life, an effect size can be determined from baseline or from any treatment point. In some embodiments, an effect size of between 0.2 to <0.49 indicates a small effect, 0.5 to 0.79 indicates a moderate effect, and 0.8 or greater indicates a large effect. These numbers are examples only and the effect size may change with treatment of certain individuals.

Administration of the MUC-1-based formulations may also be useful in preventing the worsening in quality of life seen over time in many cancer patients. For example, in some embodiments, administration of a MUC-1-based formulation such as the BLP25 liposomal vaccine may result in quality of life indexes that essentially remain unchanged or do not reach the level of worsening or improving quality of life.

In one embodiment, the present invention encompasses improving or maintaining the quality of life or improving or stabilizing lung cancer symptoms in an individual diagnosed with NSCLC by determining the individual's TOI or LCS scores before, during, and after treatment with the BLP25 MUC-1-based formulation described herein.

XVIII. Decreasing PSA Doubling Time

In some embodiments, treatment of individuals with prostate cancer with the MUC-1-based formulations of the invention will result in a decrease in PSA concentrations, a stabilization of PSA concentrations, or a decrease in PSA doubling time. Generally, the effect of the MUC-1-based formulations on PSA concentrations or PSA doubling time may be measured at any time. For example, although PSA concentrations following treatment may be compared to a baseline value, the PSA concentration may also be compared between treatment points or between a specific treatment point and the end of treatment. In certain embodiments, the PSA response will be confirmed during treatment.

XIX. Evaluation of Treatment Using Immune Function

In some embodiments, the response of individuals to MUC-1-based formulations will be measured using tests of immune function, such as a T-cell proliferation response assays. In some embodiments, the results from T-cell proliferation response assays will be used to determine whether the MUC-1-based formulation treatment is effecting an individual. Results from these assays may also be used to determine individual response to the formulations during different time points during the course of the treatment.

Assays to measure proliferative T-cells are not particularly limiting and can be accomplished by any method known in the art. Comparison of the T-cell proliferation response may be undertaken to compare pre-treatment versus post-treatment response as well as to compare immune responses within treatment.

XX. Other Cancers

The present invention also encompasses the treatment of other cancers in addition to NSCLC and prostate cancer with the MUC-1-based formulations described herein.

Any individual who has a cancer that expresses MUC-1 may be targeted for treatment with the MUC-1-based formulations. For instance, an individual with a mucinous type cancer, or an adenocarcinoma that expresses a MUC-1 protein may be targeted for treatment with the BLP25 liposome vaccine. Examples of adenocarcinomas include, but are not limited to ovarian cancer, liver cancer, e.g., invasive cholangiocarcinomas of the liver, colon cancer, breast cancer, pancreatic cancer, e.g., invasive ductal carcinomas of the pancreas, and kidney cancer, and multiple myeloma. Other cancers include cervical cancer, uterine cancer, and leukemia. Another cancer that expresses MUC-1 is head and neck cancer.

The examples below are intended to illustrate but not limit the invention. While they are typical of how the methods of the present invention might be used, other methods, which conform to the spirit of the invention, are anticipated and may be used. Throughout the specification, any and all references to a publicly available document, including a U.S. patent, are specifically incorporated by reference.

Example 1

Phase II Study of Liposomal MUC1 Vaccine for Treatment of NSCLC

This example demonstrates the effects of a L-BLP25 vaccine on the treatment of subjects with either stage IIIB locoregional or stage IV NSCLC.

Patients treated with the L-BLP25 vaccine demonstrated increased survival rates. Furthermore, a clear advantage of the addition of BLP25 liposome vaccine to best supportive care compared to best supportive care alone was demonstrated by the maintenance in stable physical well-being throughout the treatment and maintenance phases of therapy and maintenance in the individuals' quality of life, as measured by the FACT-L total score and the Trial Outcome Index.

Methods:

The controlled, open-label Phase IIb trial enrolled 171 patients. Of the 171 patients enrolled, 65 had IIIB locoregional disease. Of these, 35 were randomized to treatment and 30 were randomized to best standard care. The groups were well balanced in terms of age and ethnicity. More female and ECOG 0 patients were randomized to treatment versus best standard care (BSC) (51.4% and 36.7%, and 40.0% and 26.7%) and more patients in the treatment arm received radiotherapy, in addition to chemotherapy, for cancer treatment prior to trial enrollment (91.4 versus 76.7%).

The L-BLP25 vaccine used in this particular experiment was a lyophilized preparation consisting of (1) 1000 μg of a BLP25 lipopeptide, e.g., a MUC-1 peptide comprising SEQ ID NO: 2, (2) 500 μg immunoadjuvant monosphoshoryl lipid A, and (3) three lipids: (i) 17.3 mg cholesterol, (ii) 3.6 mg dimyristoyl phosphatidylglycerol, and (iii) 29.1 mg dipalmitoyl phosphatidylcholine forming a liposomal product.

All patients in the L-BLP25 arm received at least five vaccinations, 96.6% of these patients completed the primary phase and 69.3% continued on to the maintenance phase of the treatment plan. Second-line therapy while on study consisted mostly of chemotherapy (second or third-line), radiotherapy, and surgery. During the primary treatment period of the study, five patients on the L-BLP25 arm and 10 patients on the BSC arm received second-line therapy. Of the patients who continued on to the maintenance period of the study, 43 patients on the L-BLP25 arm and 45 patients on the BSC arm received second-line therapy.

To enhance the antigenic stimulation of a greater number of draining lymph nodes, the vaccine was administered to four anatomical sites. The 1000 μg dose of L-BLP25 was given in four 0.5 mL subcutaneous injections, with each injection containing one-fourth of the total dose. The sub-doses were administered in the deltoid or triceps region of the upper arms, and the left and right anterolateral aspects of the abdomen.

Generally, as used in this example, survival time is defined as the time from the date of randomization to the date of death. For patients alive or lost to follow-up at time of analysis, the interval between date of randomization and date on which the patient was last known alive was calculated and used as a censored observation in the analysis. In this example, survival was monitored at three-month intervals for 12 months after completion of patient accrual.

A FACT-L QoL questionnaire was administered to all patients at specific time points. The QoL analysis included evaluation of mean FACT-L individual change scores from baseline to week four and week eight, graphic representation of QoL scores over time, and area under the curve analysis for total and subscale scores. The effect size of the quality of life changes between treatment arms was determined from baseline. An effect size between 0.2 to <0.49 indicates a small effect, 0.5 to 0.79 indicates a moderate effect, and 0.8 or greater indicates a large effect.

Figure 2:
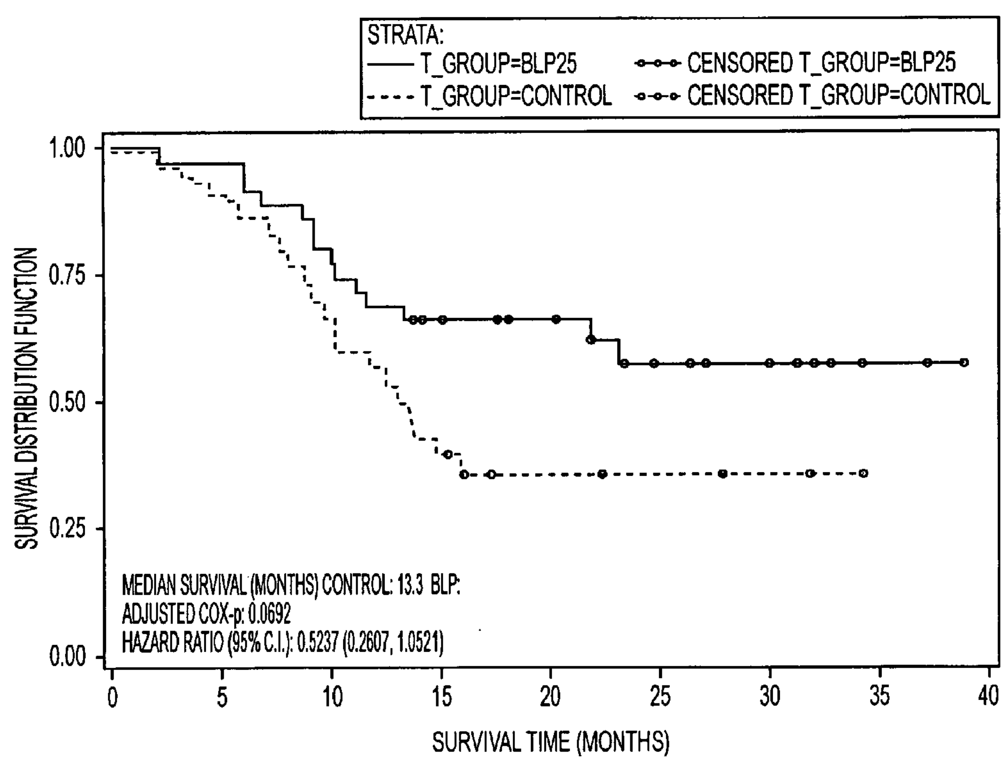
FIG. 2 is a graph demonstrating survival analysis for stage IIIB locoregional patients with NSCLC. The survival analysis for the two groups of patients (treatment and BSC) includes the survival distribution function of patients treated with BLP25 liposomal vaccine versus patients treated only with best supportive care. See example 1 below.
Figure 3:
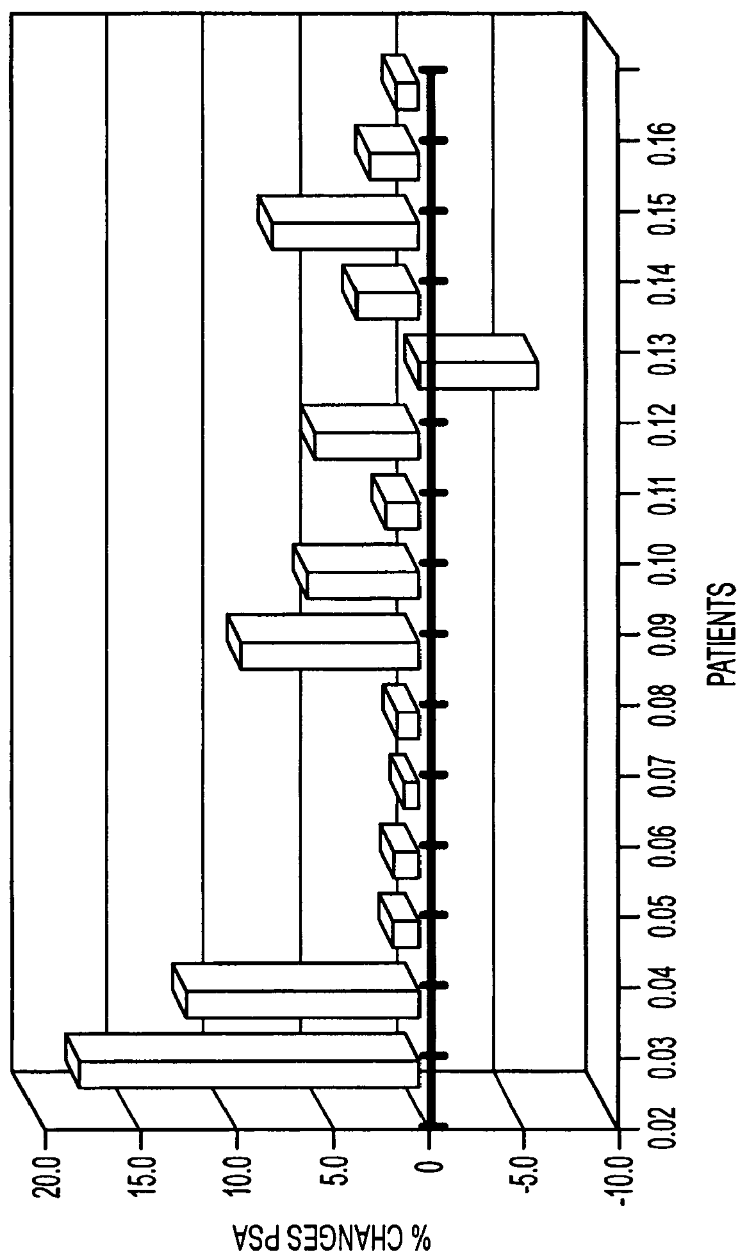
FIG. 3 is a graph depicting the percentage change in prostate-specific antigen ("PSA") doubling time for different patients who had received a dose of BLP25 liposomal vaccine. See example 3 below.

Results:

As shown in FIG. 2, the observed two-year survival for stage IIIB locoregional patients is 60% for the vaccine arm versus 36.7% for the control arm, demonstrating a significant increase in life expectancy of 23.3%. In the overall patient population, the two-year survival is 43.2% for the vaccine arm versus 28.9% for the control arm, demonstrating an increase in life expectancy of 14.3%. See FIG. 1. The median survival of stage IIIB locoregional patients undergoing only best standard care was similar to the overall median survival of the entire group undergoing best standard care at 13.3 months. In contrast, the overall median survival for the stage IIIB locoregional patients undergoing treatment with L-BLP25 has remained unmet with a minimum median of 24 months, demonstrating an increase in life expectancy of at least 10.7 months. This is surprising and unexpected, as prior to the introduction of the MUC-1 compositions of the invention, no viable treatment options for this category of patients could produce such results.

Regarding the quality of life, a clear advantage for the L-BLP25 arm compared to the BSC arm was demonstrated. More patients in the L-BLP25 arm showed either a clinically meaningful improvement or did not change compared to patients in the BSC arm. In the BSC only arm, more patients demonstrated a clinically meaningful worsening in the Trial Outcome Index (TOI).

Method:

Stage IIIB locoregional (LR) disease and stage IIIB with malignant pleural effusion (PE)/IV subgroup comparison analysis between treatment and BSC only patients was performed for the FACT-L total score, the various subscales, and TOI using a T-test. A negative Total/TOI change score indicates a worsening in QoL, whereas a positive Total/TOI change score indicates an improvement. The subgroup analysis indicates a better QoL for stage IIIB LR patients treated with L-BLP25. This is consistent with previous data demonstrating a clinically meaningful improvement in survival in stage IIIB LR patients treated with BLP25 (p=0.0692).

The results of the Quality of Life comparisons are shown in Table 1 below:

TABLE 1

FACT-L Quality of Life Comparison in NSCLC Study

| QoL | IIIBLR TX | IIIBLR BSC | P | IIIBPE/TV TX | IIIBPE/IV BSC | P |
|---|---|---|---|---|---|---|
| FACT-L Total Score | | | | | | |
| Δ From Baseline week 19 | 0.6 ± 12.1 | −7.5 ± 12.7 | .027 | −0.2 ± 13.2 | −8.6 ± 22.2 | .072 |
| Δ From Baseline week 31 | 2.9 ± 14.2 | −8.0 ± 9.0 | .008 | −2.4 ± 10.3 | −0.7 ± 17.0 | .737 |
| TOI | | | | | | |
| Δ From Baseline week 19 | 0.5 ± 8.2 | −6.5 ± 10.9 | .014 | −1.0 ± 10.6 | −6.6 ± 15.0 | .110 |
| Δ From Baseline week 31 | 1.2 ± 10.2 | −6.5 ± 8.3 | .016 | −1.3 ± 8.7 | −2.4 ± 10.5 | .761 |

Study Design

Week −2: Administration of a FACT-L QoL questionnaire.

Week −2: Patients were randomized to either L-BLP25 plus best standard of care or to best standard of care alone (best standard of care includes palliative radiotherapy and/or second line chemotherapy according to current standard clinical practice and may also include psychosocial support, analgesics and nutritional support).

Week −2: Pretreatment evaluation (complete history, physical examination, and clinical laboratory studies). Evaluations of other potential disease sites were conducted, if clinically warranted, to rule out progressive disease in other areas. Women of childbearing potential were required to have a negative pregnancy (HCG) test before treatment.

Day −3: Treatment arm patients received a single intravenous dose of 300 mg/m$^2$ cyclophosphamide.

Weeks 0 to 7: L-BLP25 vaccinations #1 to #8 (primary treatment period). Patients on the L-BLP25 arm had vital signs assessed and previous injection sites inspected prior to each L-BLP25 treatment. Vital signs were also monitored one-hour following each L-BLP25 treatment. Patients were given diary cards following each vaccination to record any adverse events and previous injection sites were evaluated at each subsequent visit. Toxicity was graded according to the CALGB Expanded Criteria.

Week 4: Treatment evaluation and safety and immunology blood work for patients in the treatment arm. FACT-L QoL Questionaire to all patients.

Week 8: Treatment evaluation (physical examination, ECOG status, vital signs, treatment site inspection for the L-BLP25 arm, and adverse events assessment). Blood samples were also drawn and analyzed for standard safety (hematology and chemistry) as well as immune response. FACT-L QoL Questionaire to all patients.

Week 19+: Maintenance vaccinations (6 week intervals) and treatment evaluations (12 week intervals). Patients on the L-BLP25 arm had treatment evaluations and safety blood work performed at each maintenance vaccination as well as an immunology profile examination one week following the first maintenance vaccination. FACT-L QoL Questionaire to all patients.

Patient Population

Inclusion Criteria

1. Men and women over the age of 18 with NSCLC whose disease was stable or who had responded to treatment following completion of their first line standard chemotherapy.

2. Eastern Cooperative Oncology Group (ECOG) performance status of ≤2, with a neturophil count≥1.5×10$^9$/L; platelet count≥100×10$^9$/L; WBC≥2.5×10$^9$/L and hemoglobin 90 g/L.

3. Expected survival of four months.

4. Understood and signed a written consent.

Exclusion Criteria

1. Surgery or immunotherapy within fours weeks prior to study entry.

2. Immunosuppressive drugs including systemic corticosteroids within three weeks prior to study entry.

3. Past or current history of neoplasm other than lung carcinoma.

4. Autoimmune disease or recognized immunodeficiency disease.

6. Clinical significant hepatic or renal dysfunction.

7. Significant cardiac disease or active infection, or patients who had had a splenectomy.

TABLE 2

Patient Characteristics of NSCLC Study

| | L-BLP25 + BSC N = 88 | BSC N = 83 | Total N = 171 |
|---|---|---|---|
| Age at Randomization: (years) | | | |
| Median | 59.5 | 59 | 59 |
| Gender: N (%) | | | |
| Female | 36 (40.9) | 40 (48.2) | 76 (44.4) |
| Male | 52 (59.1) | 43 (51.8) | 95 (55.6) |
| ECOG Performance Status: N (%) | | | |
| 0 | 31 (35.2) | 22 (26.5) | 53 (31.0) |
| 1 | 53 (60.2) | 57 (68.7) | 110 (64.3) |
| 2 | 4 (4.5) | 4 (4.8) | 8 (4.7) |

TABLE 2-continued

| Patient Characteristics of NSCLC Study | L-BLP25 + BSC N = 88 | BSC N = 83 | Total N = 171 |
|---|---|---|---|
| Disease stage: N (%) | | | |
| IIIB LR | 35 (39.8) | 30 (36.1) | 65 (38) |
| IIIB MPE or IV | 53 (60.2) | 53 (63.9) | 106 (62) |
| Response to First-line Therapy: N (%) | | | |
| Stable Disease | 39 (44.3) | 38 (45.8) | 77 (45.0) |
| Clinical Response (PR or CR) | 49 (55.7) | 45 (54.2) | 94 (55.0) |

Example 2

T-Cell Proliferation Response Assays

This example demonstrates that the MUC-1 formulations of the invention were directly responsible for the increase in median survival shown in Example 1.

Lymphoproliferation assays were performed using the patients enrolled in the study of Example 1 to monitor MUC1 antigen specific TH response (proliferation of helper T-cells) prior to and following vaccinations to measure the dynamics of the patient's anti-MUC1 cellular immune response. T-cell proliferation assays were performed on patients in the L-BLP25 arm both pre-immunization and at several time points post immunization.

Of the patients in the L-BLP25 arm, 78 were evaluated for a T-cell proliferative response. Sixteen patients were determined to have a positive MUC1 specific T-cell proliferative response that was induced by the L-BLP25 vaccine (the response did not exist pre-immunization). Of the sixteen patients who developed an immune response, two had stage IIIB locoregional disease, with the remaining patients having stage IV disease. The median survival of the patients on the L-BLP arm with a positive proliferative response was 27.6 months while those patients with a negative proliferative response had a median survival of 16.7 months. These results demonstrate that the MUC-1 formulation of the invention was directly responsible for the increase in median survival of life expectancy of 10.9 months.

Example 3

Phase II Study of Liposomal MUC1 Vaccine in PSA Failures Post-Radical Prostatectomy (RP)

This example shows the immunotherapeutic effects of L-BLP25 vaccine on the PSA levels in men with rising PSA following radical prostatectomy.

At the end of the primary treatment period (week 8), 8/16 patients had stable PSA. One patient maintained stable PSA through to the end of the study period (week 49). There was a noted prolongation in PSA doubling time ("PSADT") for all but one patient enrolled. The doubling time is the length of time it takes for an individual's PSA level to double and is a factor used to predict survival following surgery in individuals with prostate cancer. The present data show that, in 6/16 patients, the doubling time exceeded 50%.

Methods:

Men with biochemical failure as evidenced by 3 rises in PSA post-prostatectomy were enrolled. This included sixteen patients, with a median age of 60, an ECOG score of 0 or 1, and median Gleason score of 7. Primary endpoints were efficacy (as measured by PSA response) and safety of a MUC1 liposomal vaccine (L-BLP25). Changes in PSA doubling time (PSADT) were also evaluated. Patients received a single intravenous dose of 300 mg/m$^2$ cyclophosphamide (CTX) followed by 8 weekly subcutaneous vaccinations with L-BLP25 containing 1,000 μg antigen (treatment). Subsequent vaccinations were given at 6-week intervals through week 49 (maintenance). PSA concentrations were measured during the treatment and maintenance phases and PSADT was calculated for these intervals and compared to PSADT prior to enrolment.

All 16 patients received CTX and 15/16 completed the treatment period. Ten patients completed the maintenance period. The most common adverse events following treatment were nausea (31%) and fatigue (25%); however, none of these adverse effects were worse than grade 1.

Results:

After induction, 8/15 evaluable patients had either stabilization or decrease in PSA (as per PSA Working Group definition). At the last on-study PSA measurement, one patient maintained a stable PSA. 6/15 patients had a >50% prolongation of PSADT compared to pre-study PSADT.

Primary endpoint evaluation of PSA stabilization or reduction in this individual population by the use of L-BLP25 vaccine was as follows:

8/16 individuals had PSA stability after primary treatment period;

1/16 individuals retained PSA stability by the end of the maintenance period; and PSADT was prolonged in 14/15 subjects by use of vaccine; 6/16 individuals had prolongation of PSADT by >50%.

Study Design:

Week −2: Pre-treatment evaluation (physical exam, PSA concentration measurement, pelvic CT, and bone scan).

Day −3: Cyclophosphamide pretreatment.

Weeks 0 to 7: L-BLP25 Vaccinations #1 to #8 (primary treatment period).

Week 8: Primary treatment period evaluation including PSA response.

Week 13: Confirmation of PSA response.

Weeks 13, 19, 25, 31, 37, 43 & 49: L-BLP25 Vaccinations #9 to #15 (maintenance period).

Week 43: Evaluation of PSA response.

Week 49: Confirmation of PSA response.

Week 50: Maintenance treatment evaluation.

Individual Population:

Inclusion Criteria

1. Radical prostatectomy at least 6 months prior to study entry.

2. Three consecutive increases in serum PSA values post-radical prostatectomy with at least a 50% increase above the post-prostatectomy nadir.

3. No evidence of malignant disease at pre-treatment evaluations as evidenced by negative pelvic CT and bone scan.

4. ECOG performance status of 0, 1.

5. Normal haematological, hepatic and renal function tests.

6. Understood and signed a written informed consent.

7. Serum testosterone within the normal range for all patients who have ever been treated with hormonal therapy for prostate cancer (i.e. neoadjuvant treatment pre-RP).

Exclusion Criteria

1. Hormonal therapy within 6 months prior to study entry.

2. Immunotherapy within 4 weeks prior to study entry.

3. Radiotherapy to the prostate bed within one year prior to study entry.

4. Treatment with immunosuppressive drugs such as cyclosporin or adrenocorticotropic hormone (ACTH) or required chronic treatment with corticosteroids.

5. Known autoimmune or immunodeficiency disease.

6. Clinically significant cardiac disease or active infection.

TABLE 3

| Patient Characteristics for Prostate Cancer Study | |
|---|---|
| Age (yrs): | |
| n | 16 |
| Mean ± S.D. | 60.4 ± 7.7 |
| Median | 60.0 |
| 25%/75% | 54.5/66.0 |
| Range | 46.0 to 74.0 |
| ECOG Performance Status: | n (%) |
| 0 | 13 (81%) |
| 1 | 3 (19%) |
| Gleason Grade: | |
| 6 | 3 (19%) |
| 7 | 10 (63%) |
| 8 | 3 (19%) |
| Initial Diagnosis to Study Entry (years): | |
| Mean ± S.D. | 3.8 ± 2.5 |
| Median | 3.2 |
| Range | 1.0 to 9.5 |
| Post-prostatectomy Nadir to Study Entry (years): | |
| Mean ± S.D. | 3.1 ± 2.3 |
| Median | 2.8 |
| Range | 0.6 to 9.1 |
| Baseline PSA μg/L: | |
| Mean | 3.8 |
| Median | 0.4 |
| 25%/75% | 0.1/0.8 |
| Treatment Received | |
| Total Number Receiving Treatment | n (%) |
| Cyclophosphamide | 16 (100.0) |
| Primary Treatment Period Vaccinations | |
| 1 | 16 (100.0) |
| 2 | 16 (100.0) |
| 3 | 16 (100.0) |
| 4 | 16 (100.0) |
| 5 | 16 (100.0) |
| 6 | 16 (100.0) |
| 7 | 15 (93.8) |
| 8 | 15 (93.8) |
| Maintenance Treatment Period Vaccinations | |
| 9 | 14 (87.5) |
| 10 | 14 (87.5) |
| 11 | 13 (81.3) |
| 12 | 12 (75.0) |
| 13 | 11 (68.8) |
| 14 | 10 (62.5) |
| 15 | 10 (62.5) |

TABLE 4

PSA VALUES
Change in PSA from Baseline to Week 8
(primary treatment period)
Per Patient

| Subject Number | Baseline PSA (μg/L) | Week 8 PSA (μg/L) | Response at Week 8 |
|---|---|---|---|
| 001 | 20.00 | Did not reach week 8 | Not Assessed |
| 002 | 35.00 | 48.00 | Progression |
| 003 | 0.07 | 0.07 | Stable PSA |
| 004 | 0.47 | 0.46 | Stable PSA |
| 005 | 0.17 | 0.14 | Stable PSA |
| 006 | 0.89 | 0.94 | Stable PSA |
| 007 | 0.36 | 0.45 | Progression |
| 008 | 0.58 | 0.79 | Progression |
| 009 | 0.10 | 0.11 | Stable PSA |
| 010 | 0.08 | 0.10 | Progression |
| 011 | 0.59 | 0.82 | Progression |
| 012 | 0.11 | 0.18 | Progression |
| 013 | 0.13 | 0.18 | Progression |
| 014 | 0.71 | 0.64 | Stable PSA |
| 015 | 1.80 | 1.90 | Stable PSA |
| 016 | 0.38 | 0.34 | Stable PSA |

Adverse Events

Total Number of Patients with Adverse Events, n (%) 14 (87.5)

Patients Reporting Adverse Events with 10% or Greater Frequency

| | |
|---|---|
| Nausea | 5 (31.3) |
| Fatigue | 4 (25.0) |
| Diarrhoea NOS (not otherwise specified) | 3 (18.8) |
| Influenza-like illness | 3 (18.8) |
| Nasopharyngitis | 3 (18.8) |
| Constipation | 2 (12.5) |
| Headache NOS | 2 (12.5) |
| Pain NOS | 2 (12.5) |

Six of sixteen patients reported no injection site reactions of any type. Nine patients reported erythema. No ulcerations occurred. No events occurred that were severe or precluded further vaccinations.

TABLE 5

PSA DOUBLING TIME

| Patient ID | Interval A PSADT (days) | Interval B PSADT (days) | PSADT Difference Between Interval A & Interval B |
|---|---|---|---|
| 002 | 173 | 476 | 175% |
| 003 | 133 | 291 | 119% |
| 004 | 345 | 393 | 14% |
| 005 | 302 | 342 | 13% |
| 006 | 172 | 185 | 8% |
| 007 | 309 | 347 | 12% |
| 008 | 173 | 332 | 92% |
| 009 | 404 | 637 | 58% |
| 010 | 508 | 595 | 17% |
| 011 | 165 | 257 | 56% |
| 012 | 241 | 97 | −60% |
| 013 | 84 | 112 | 33% |
| 014 | 479 | 844 | 76% |
| 015 | 227 | 288 | 27% |
| 016 | 344 | 385 | 12% |
| Mean | 271 | 372 | 44% |

Interval A = Prestudy (from the first of 3 consecutive rising prestudy PSA's prior to study entry to baseline)
Interval B = Maintenance (from Week 8 to end of study)

Example 4

Tumor Marker CA27.29

FIG. 1 lists the frequency distribution of patient CA27.29 values by visit, arm (BLP25 or Control), and normal/abnormal level. Determination of serum levels of MUC1 (CA27.29) was performed on baseline samples of 166 patients (there was no data generated for 4 patients on BLP25 arm (3—no sample received; 1—improper labelling) and 1 patient on control arm (1—data not received for entry) and on post 8 immunization samples of 153 patients. No significant differences are seen between the arms by the CA27.29 levels.

Figure 5:
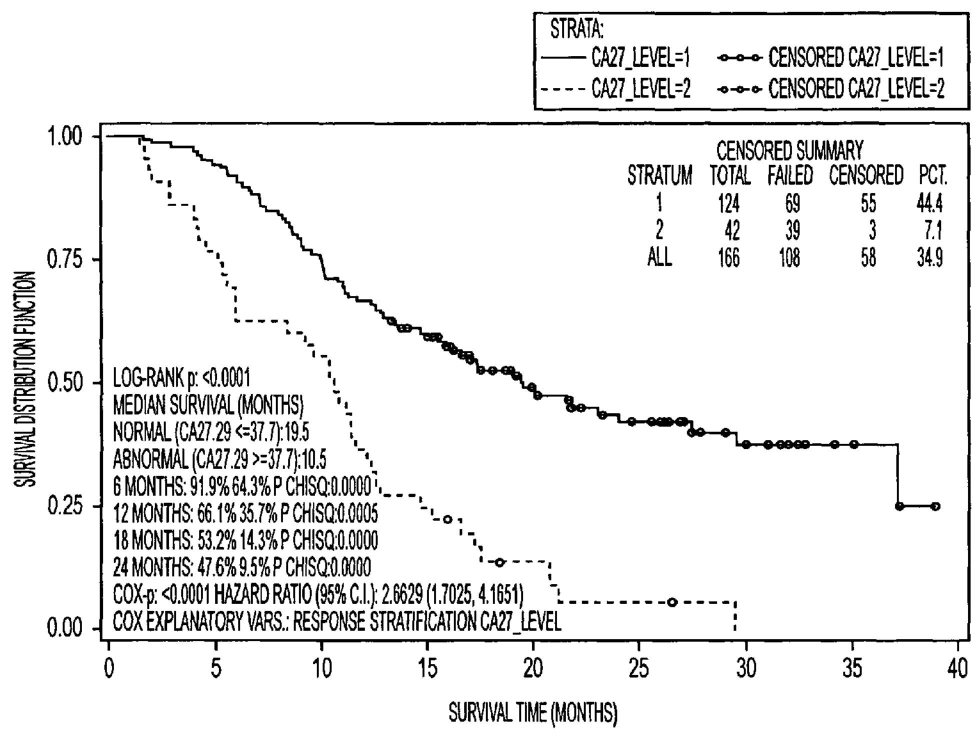
FIG. 5 displays the survival curve for patients with normal levels of the antigen at baseline compared to those patients who had abnormal levels.

FIGS. 5-9 display the Kaplan-Meier Curves of survival duration by CA27.29 (MUC1). FIG. 5 displays the survival curve for patients with normal levels of the antigen at baseline compared to those patients who had abnormal levels. The upper limit of normal for serum levels of MUC1 as determined in this assay (Truquant® BR Radioimmunoassay, based on sera from 1004 healthy female donors) is 37.7 U/ml. Levels of serum MUC1 that were greater than 37.7 U/ml were considered abnormal. There were 124 patients at baseline with normal levels of CA27.29 (63 in the BLP25 arm and 61 in the control arm) and 42 with abnormal levels (21 in the BLP25 arm and 21 in the control arm). The median survival of those patients having normal levels of CA27.29 at baseline was 19.5 months while the median survival of those having abnormal levels was 10.5 months (Cox p<0.0001).

Figure 6:
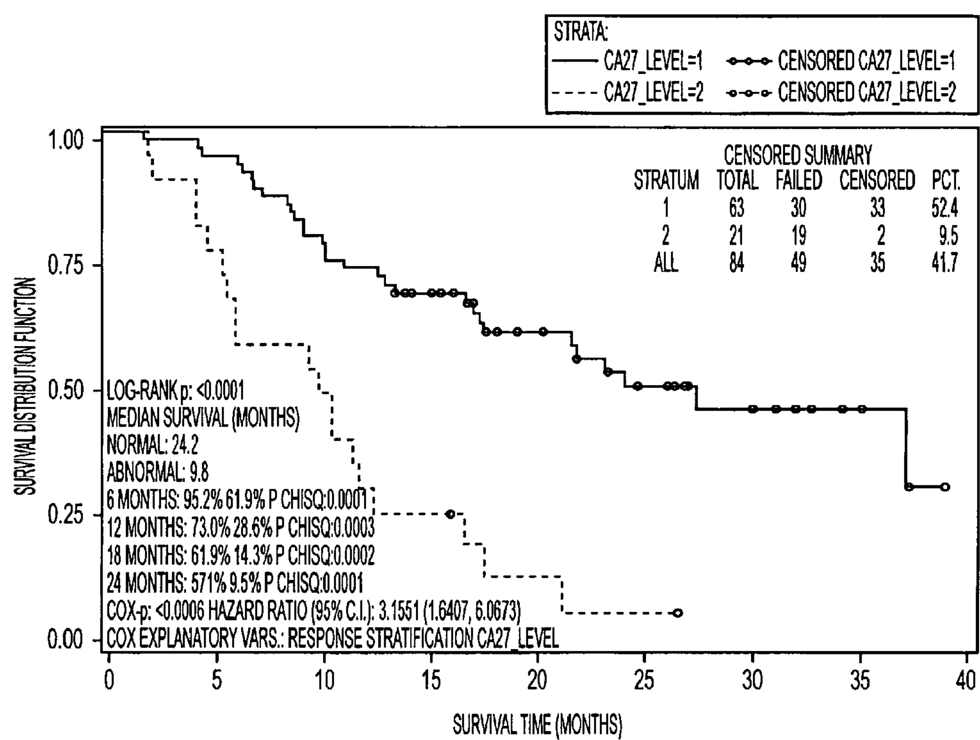
FIG. 6 shows median survival of those patients with normal levels of CA27.29 was 24.2 months while that of patients with abnormal levels was 9.8 months (Cox p=0.0006).
Figure 7:
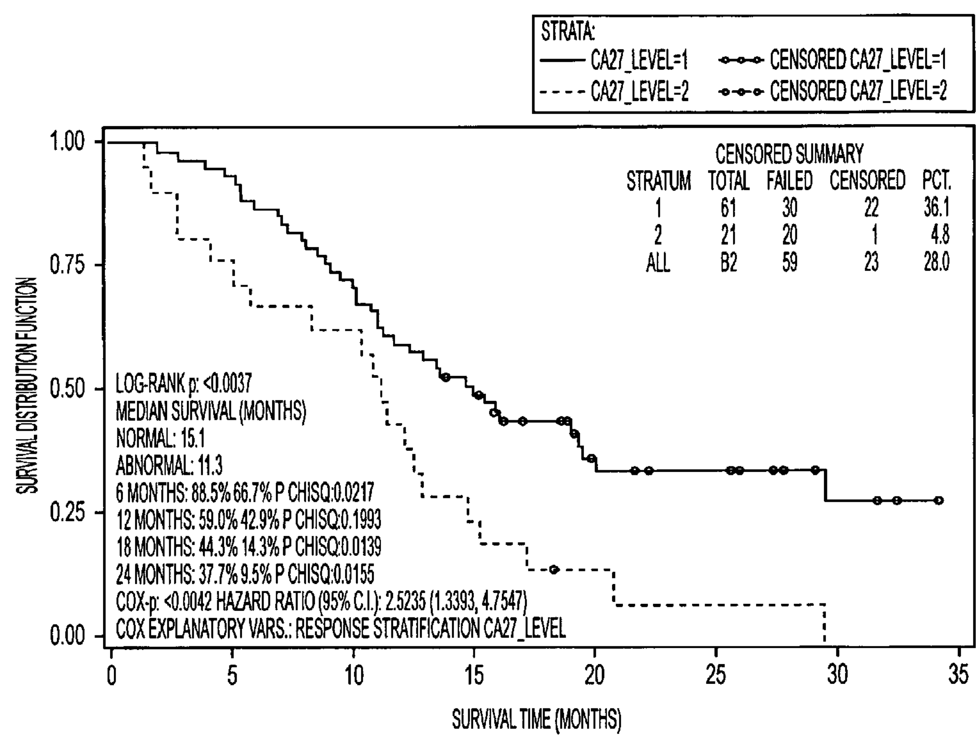
FIG. 7 shows data from the control arm where the median survival of patients with normal levels of CA27.29 was 15.1 months as compared to 11.3 months for those with abnormal CA27.29 levels (Cox p=0.0042).

FIGS. 6 and 7 illustrate the survival of patients in each arm based upon whether they have normal or abnormal CA27.29 levels at baseline. In the BLP25 arm (FIG. 6), median survival of those patients with normal levels of CA27.29 was 24.2 months while that of patients with abnormal levels was 9.8 months (Cox p=0.0006). In the control arm (FIG. 7), the median survival of patients with normal levels of CA27.29 was 15.1 months as compared to 11.3 months for those with abnormal CA27.29 levels (Cox p=0.0042).

Figure 8:
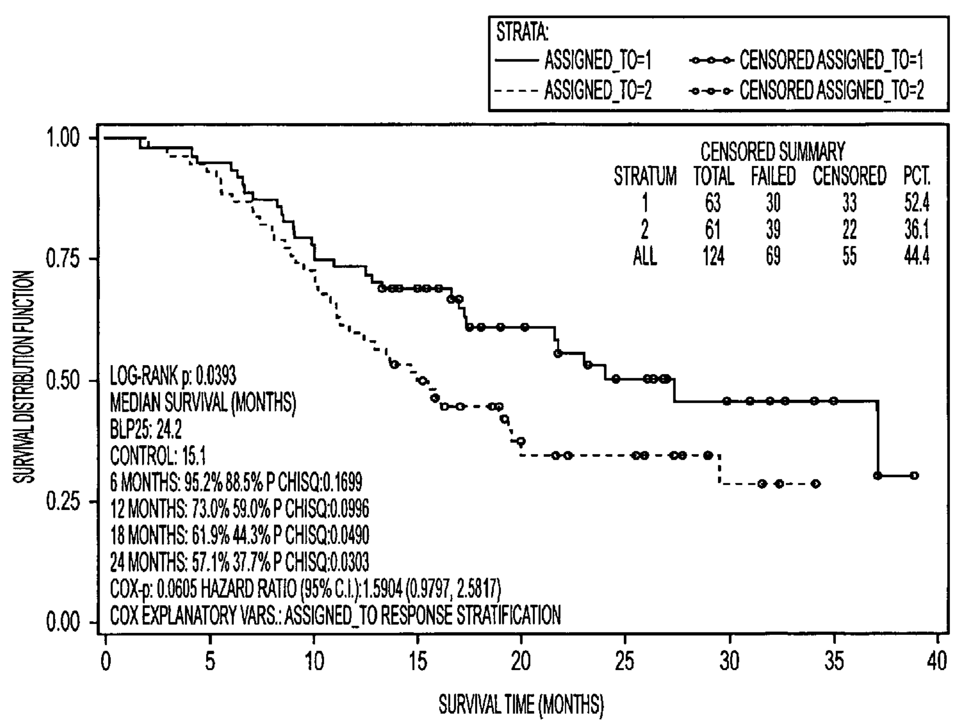
FIG. 8 shows data of patients with pre-existing normal levels of CA27.29 in the BLP25 arm had a median survival of 24.2 months as compared to those patients in the Control arm who had a median survival of 15.1 months (Cox p=0.0605).
Figure 9:
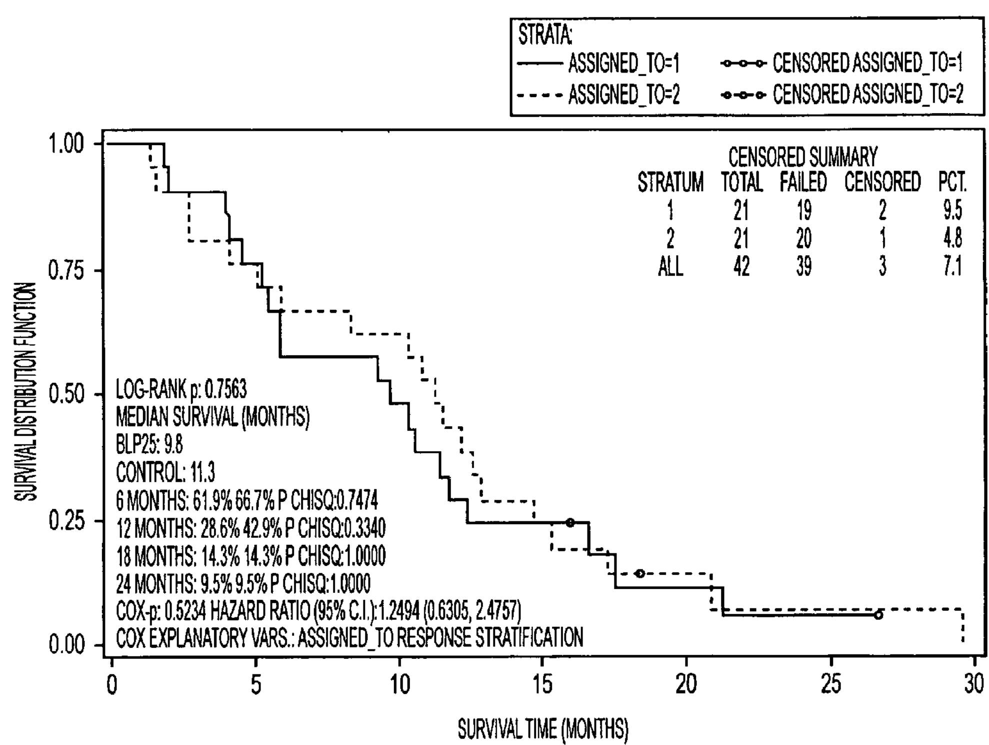
FIG. 9 shows that the patients with pre-existing abnormal levels of CA27.29 in the BLP25 arm had a median survival of 9.8 months and those patients on the control arm had a median survival of 11.3 months (Cox p=0.5234).

FIGS. 8 and 9 show the differences in survival of patients in Arm A (BLP25) versus those in Arm B (Control) based on whether they have normal or abnormal pre-immunization CA27.29 serum levels. As illustrated in FIG. 8, patients with pre-existing normal levels of CA27.29 in the BLP25 arm had a median survival of 24.2 months as compared to those patients in the Control arm who had a median survival of 15.1 months (Cox p=0.0605). In FIG. 9, the patients with pre-existing abnormal levels of CA27.29 in the BLP25 arm had a median survival of 9.8 months and those patients on the control arm had a median survival of 11.3 months (Cox p=0.5234).

Figure 10:
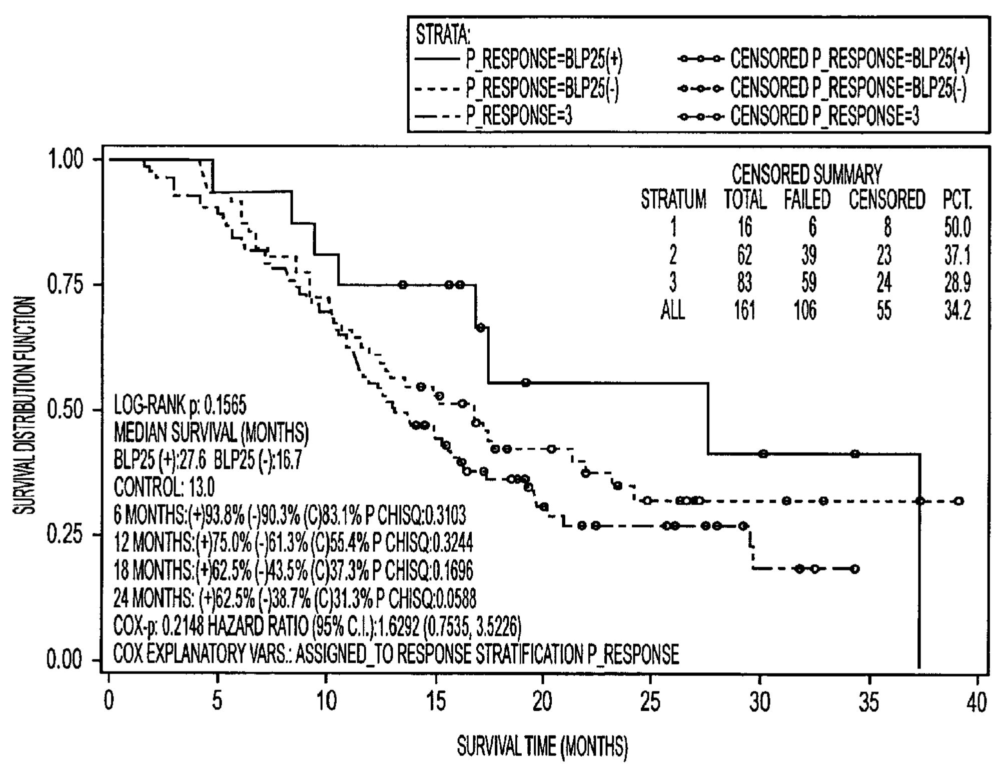
FIG. 10 shows the Kaplan-Meier Curves of survival duration by T cell proliferation.

FIG. 10 shows the Kaplan-Meier Curves of survival duration by T cell proliferation. T-cell proliferation assays were performed on patients in Arm A (BLP25) both pre-immunization and at several time points post immunization. These patients were then listed as having a positive or negative response if one or more of the time points showed a response that was different than the response at the pre-immunization time point. Of the patients on the BLP25 arm, 78 were evaluated for a T cell proliferative response. Sixteen patients where determined to have a positive MUCI specific T cell proliferative response that was induced by the L-BLP25 vaccine. The Kaplan Meier Survival Curve (FIG. 10) shows three patient populations: the control arm, the positive proliferators on the BLP25 arm and the negative proliferators on the BLP25 arm. The median survival of those patients on the BLP25 arm with a positive proliferative response was 27.6 months while those patients with a negative proliferative response had a median survival of 16.7 months; and patients on the control arm had a median survival of 13 months (Cox p=0.2148).

Example 5

HLA Typing

HLA typing was performed on all patients in Arm A (BLP25) and in Arm B (control). This typing was done to consider the possibility that the HLA Class I and II alleles that a patient expresses may be of importance to the efficacy of the vaccine. HLA typing was performed by DNA analysis not serology and the nomenclature used is that for DNA. For each arm, the % frequency and the n for a given allele were determined. For survival analysis, HLA alleles that had an n>_ 19 in either arm were chosen. Additionally the analysis was performed for HLA 11 as there is a known MUCI CTL epitope for this haplotype.

FIG. 11 illustrates the survival analyses that were performed for the chosen HLA types between treatment arms. The table lists the haplotype/allele, the total number of patients with that haplotype (each patient has more than one haplotype), the number of patients with that type on the BLP25 and Control arms, the median survival for patients with those haplotypes in the BLP25 and Control arms and the statistical significance by Log-Rank test and Cox H. R. analyses when comparing the treatment.

Figure 12:
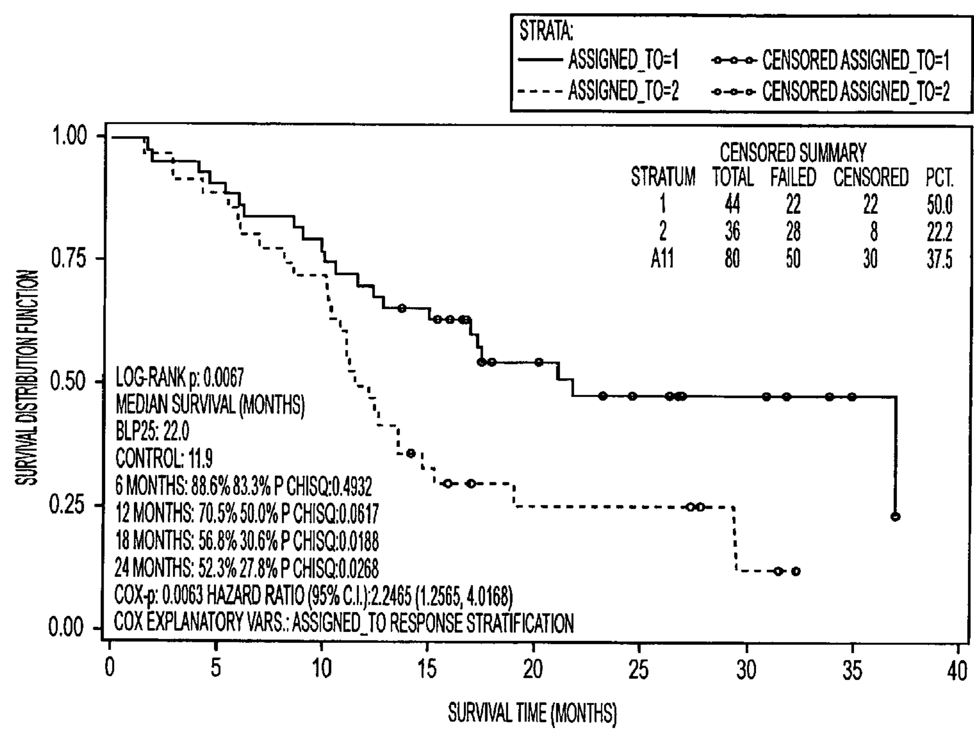
FIG. 12 shows the survival of patients with HLA A02 in each of the study arms.
Figure 13:
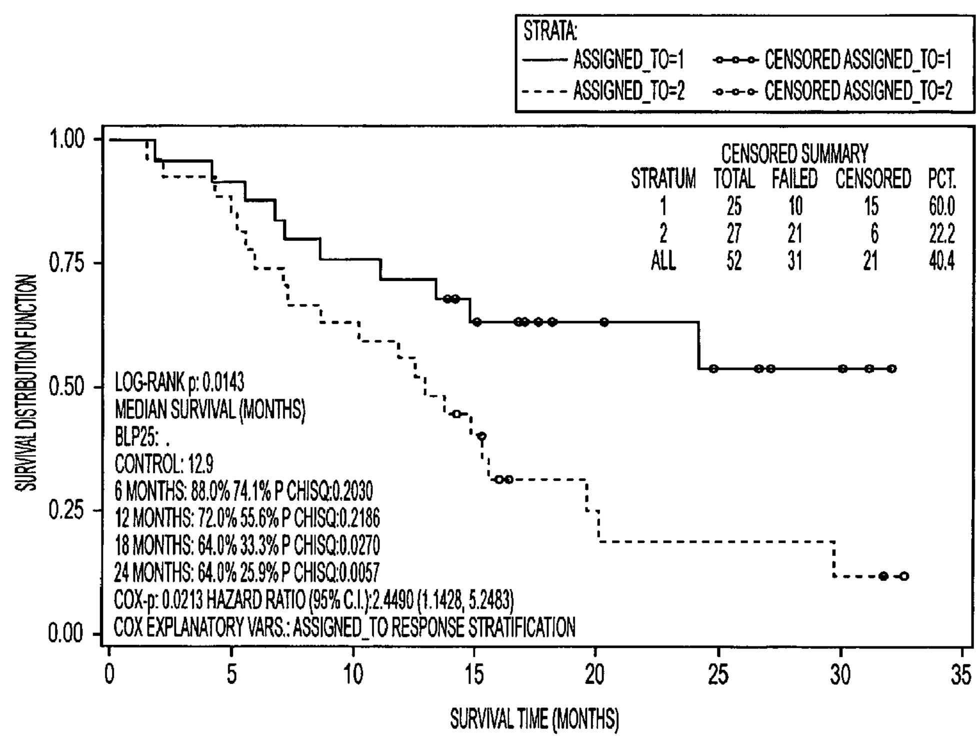
FIG. 13 demonstrates the differences in survival between the two arms in patients with the DQB 1-05 allele.
Figure 14:
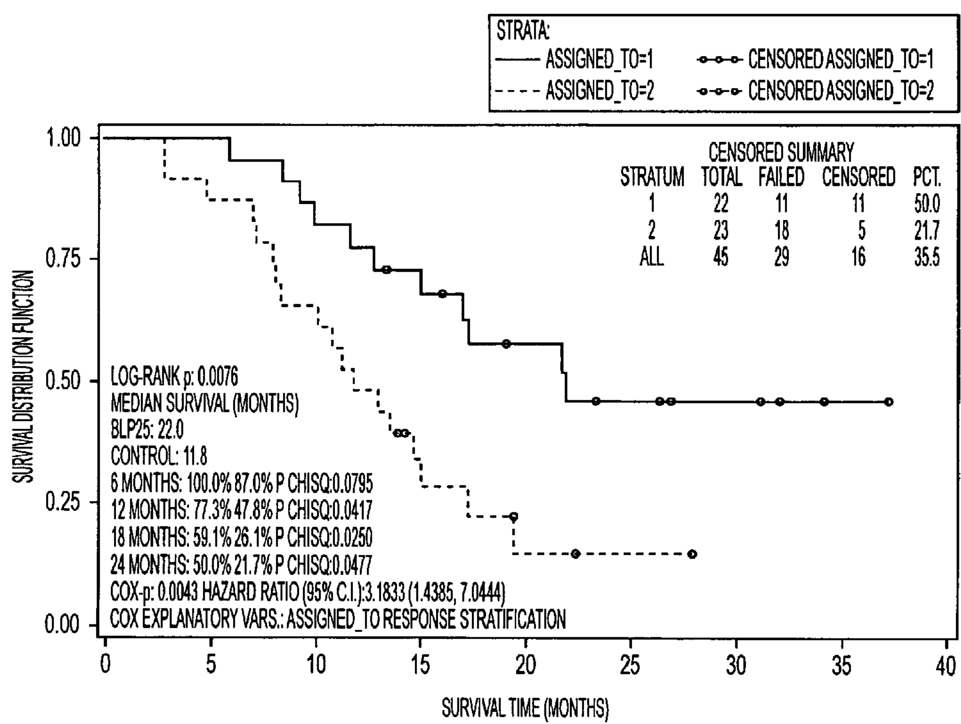
FIG. 14 displays the survival of patients in both arms who have the DRB1-04 haplotype.

FIGS. 12-16 illustrate the results of the Kaplan-Meier Survival analyses for a few of the HLA alleles. These analyses were corrected for response stratification and staging at study entrance in the Cox H. R. analysis. FIG. 12 shows the survival of patients with HLA A02 in each of the study arms. There were 44 patients with this type in the BLP25 arm and 36 patients in the Control arm. HLA A02 patients on BLP25 arm had a median survival of 22 months compared to a median survival of 11.9 months for the HLA A02 patients on the control arm (Cox p=0.0063). FIG. 13 demonstrates the differences in survival between the two arms in patients with the DQB 1-05 allele. The median survival of patients with this allele in the BLP25 arm (n=25) has not yet been reached whereas the median survival of those DQB1-05 patients in the control arm (n=27) is 12.9 months (Cox p=0.0213). FIG. 14 displays the survival of patients in both arms who have the DRB1-04 haplotype. There were 22 patients in the BLP25 arm with this haplotype and 23 patients on the control arm. Median survival was 22 months for those patients on the BLP25 arm and 11.8 months for those patients on the control arm (Cox p=0.0043).

Figure 15:
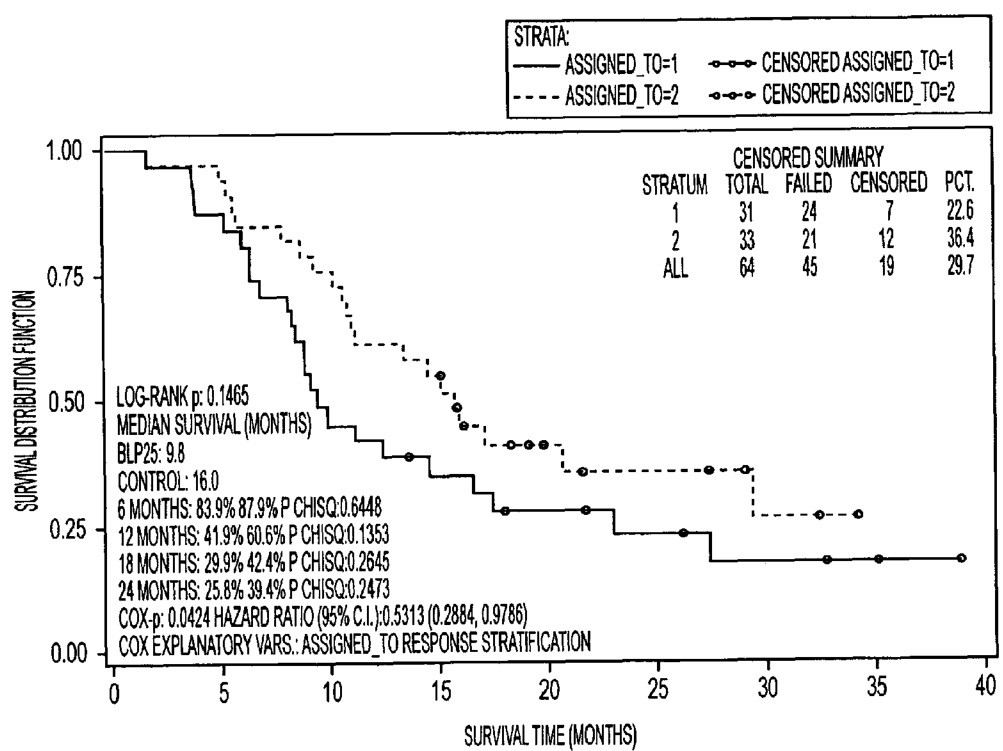
FIG. 15 shows another survival curve for patients in both arms who have the DQB 1-02 allele.

FIG. 15 shows another survival curve for patients in both arms who have the DQB 1-02 allele. Patients with this allele in the BLP25 arm (n=31) had a median survival of only 9.8 months while those in the control arm had a median survival of 16 months (Cox p=0.0424).

Figure 17:
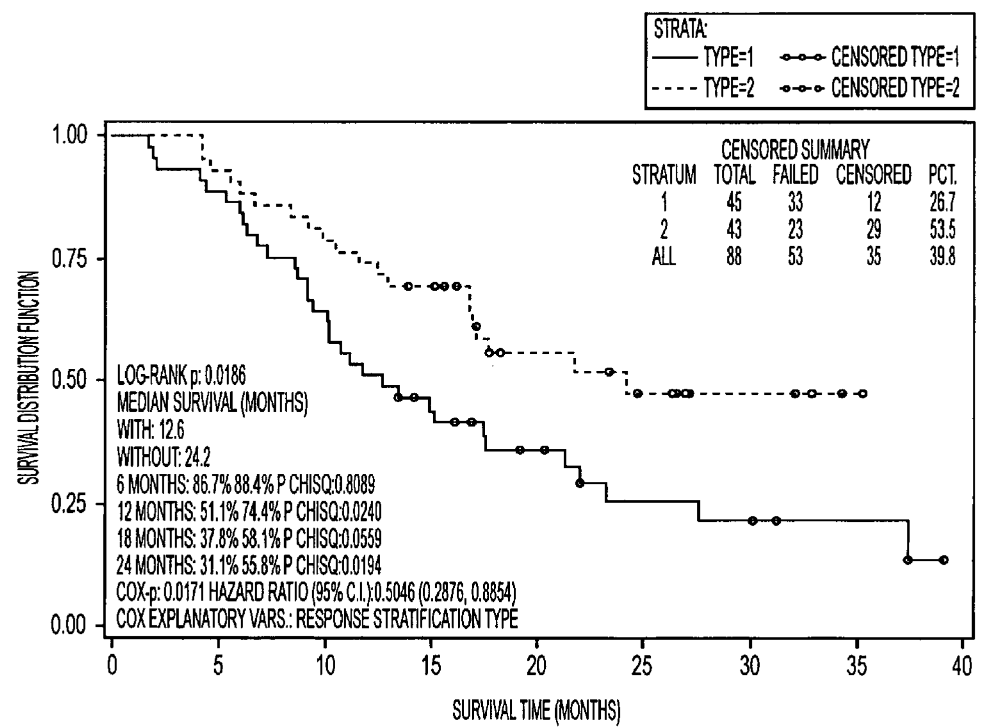
FIG. 17 shows Kaplan-Meier Survival curves for patients in the BLP25 arm only who have the CW07 allele (n=45) versus those patients who do not have the allele (n=43).

FIG. 16 illustrates additional survival analyses within the treatment arms for the same haplotypes listed in FIG. 17. The first half of the table lists the haplotype, the number of patients in the BLP25 arm that are positive and negative for the haplotype, The Log-Rank and Cox H. R. p values, and the median survivals of the patients in the BLP25 arm who are positive and negative for that haplotype. The second half of the table gives the same information for those patients on the control arm.

Figure 18:
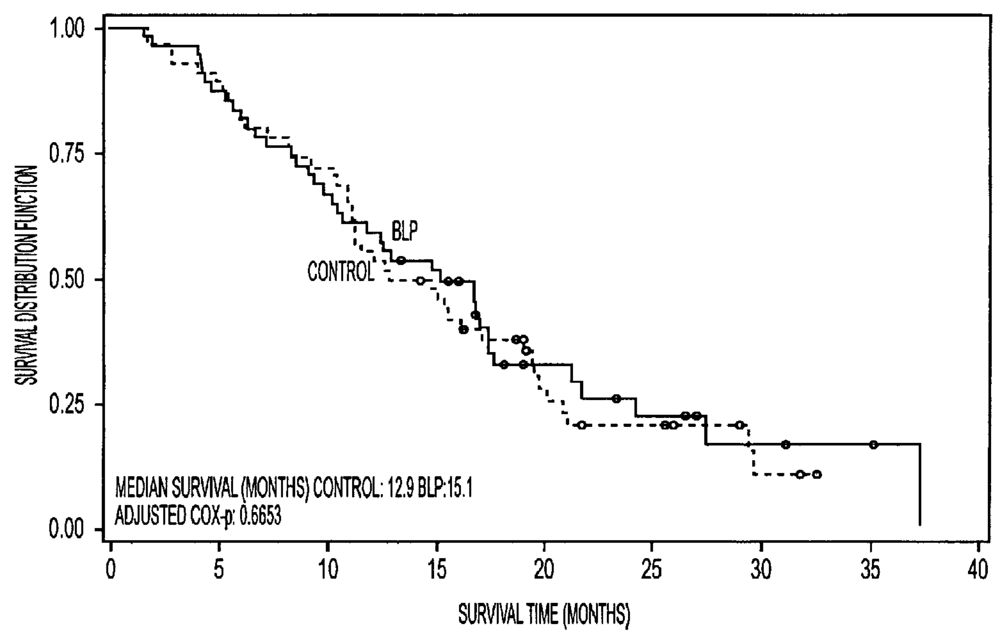
FIG. 18 shows survival by treatment arm of patients with stage IIIB malignant pleural effusion or stage IV disease at study entry.
Figure 19:
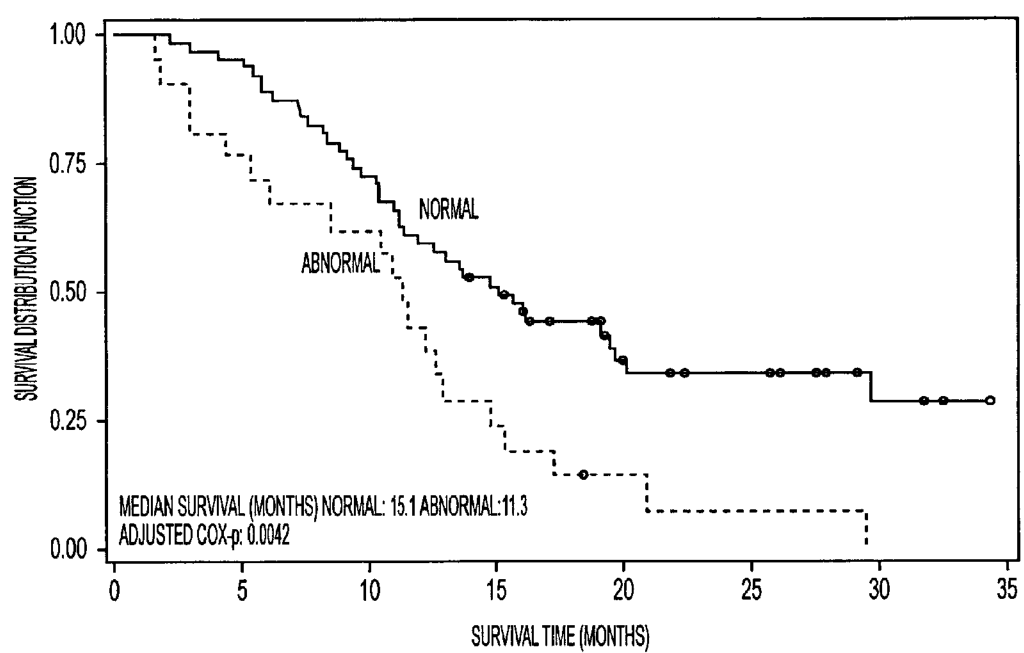
FIG. 19 shows survival in terms of baseline CA27.29 normal vs. abnormal (control arm).
Figure 20:
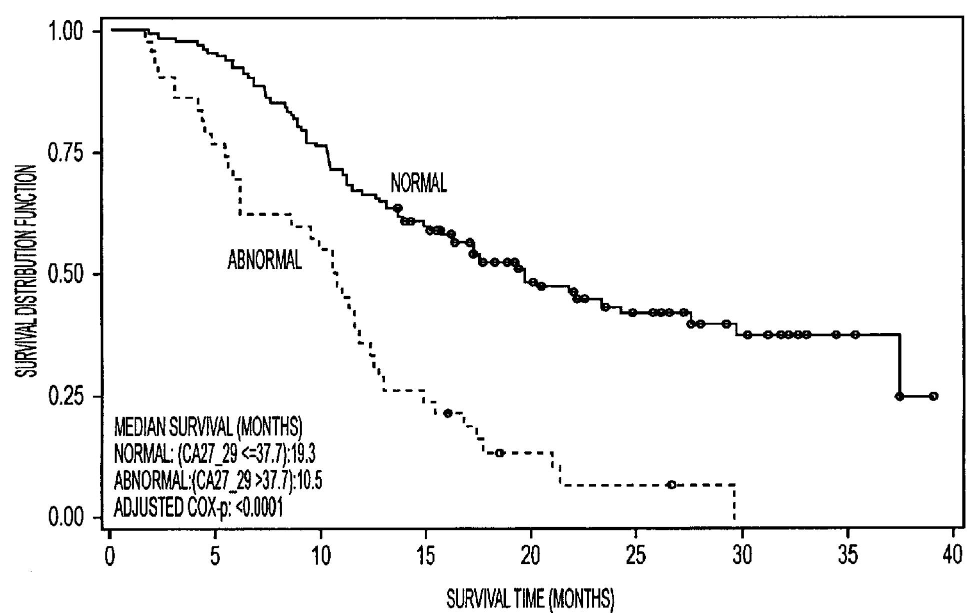
FIG. 20 shows overall survival baseline CA27.29 normal vs. abnormal.
Figure 21:
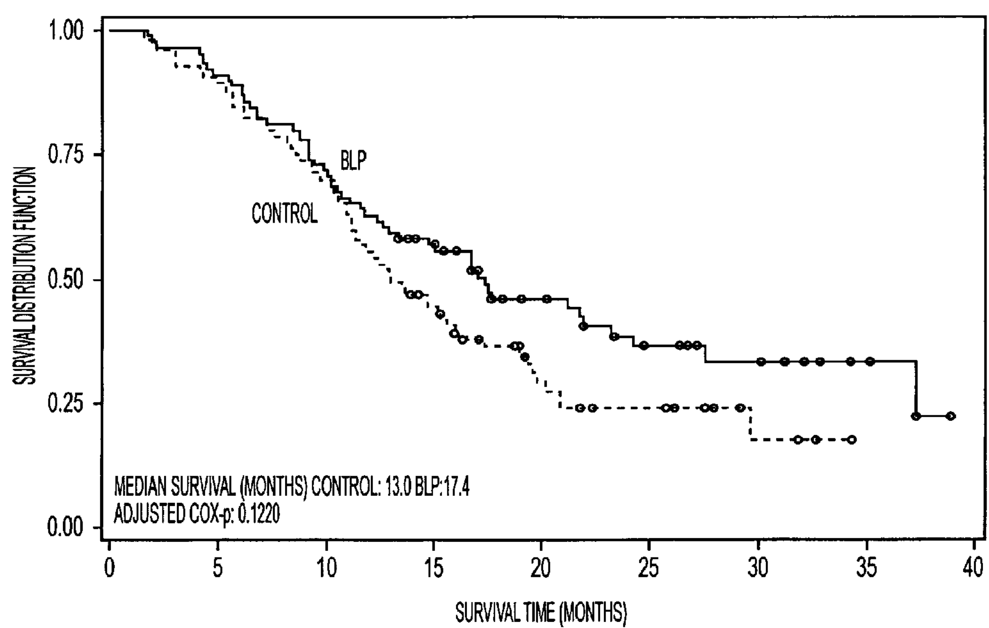
FIG. 21 shows overall survival by treatment arm.
Figure 22:
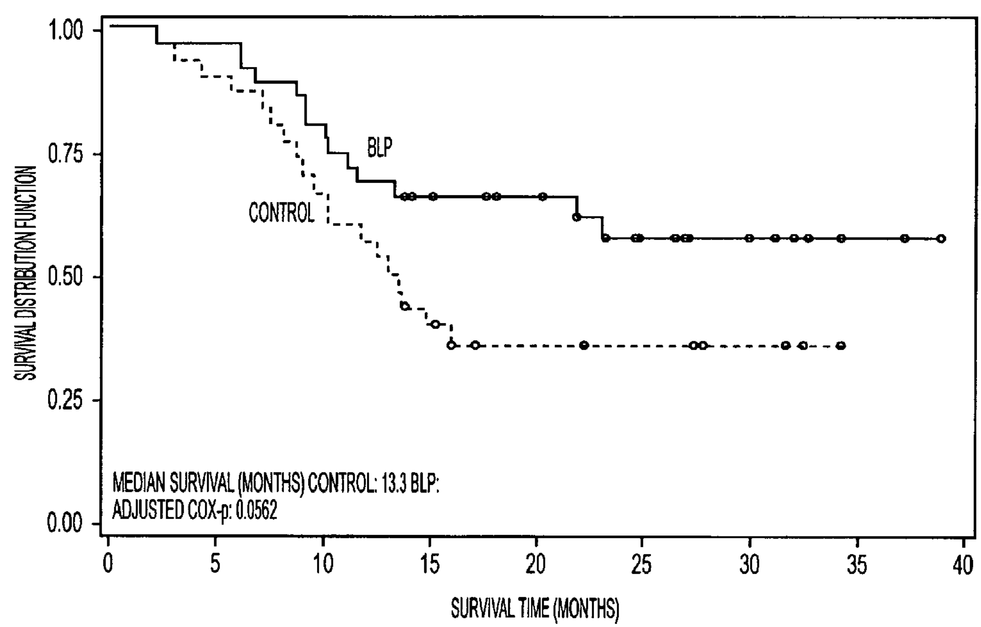
FIG. 22 shows survival by treatment arm of patients with stage IIIB locoregional disease at study entry.
Figure 23:
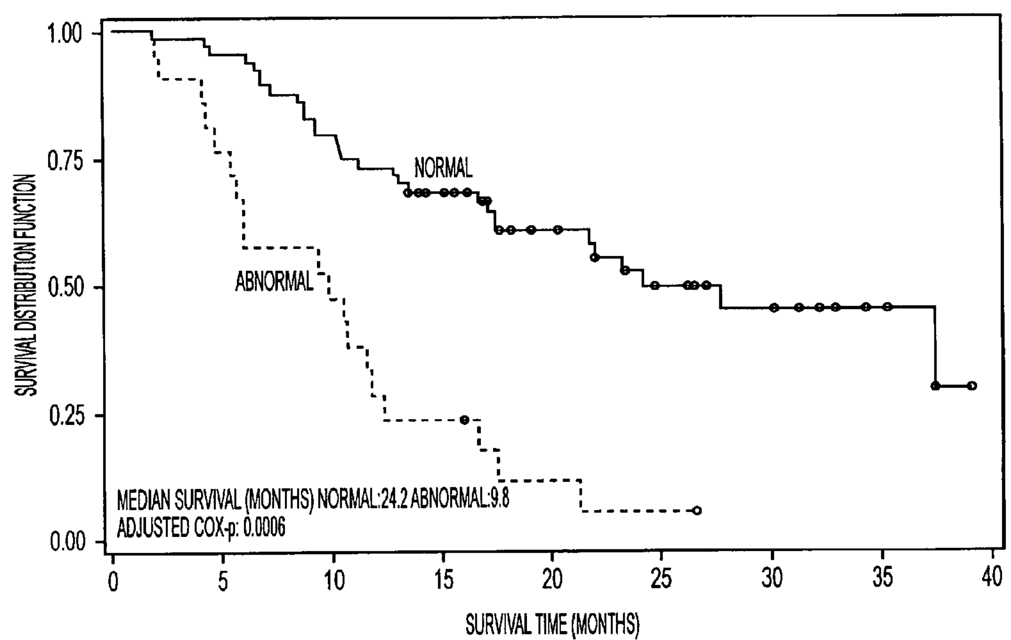
FIG. 23 survival in terms of baseline CA27.29 normal vs. abnormal (BLP arm).

The last Kaplan-Meier Survival curve (FIG. 18) displays patients in the BLP25 arm only who have the CW07 allele (n=45) versus those patients who do not have the allele (n=43). The median survival of the patients with the CW07 allele on the BLP25 arm had a median survival of only 12.6 months while those on the arm with out the allele had a median survival of 24.2 months (Cox p=0.0171). There was no real difference in the survival of patients on the control arm with and without the CW07 allele (Graph not shown). In addition, there was no real difference in survival of patients in the BLP25 arm who had the CW07 allele and those on the control arm who had the allele (data not shown).

As will be understood, all ranges disclosed herein also encompass any and all possible subranges and combinations of subranges thereof. Thus, any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood, all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

Also, where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents and publications disclosed herein are specifically incorporated by reference thereto. Unless otherwise specified, "a" or "an" means "one or more".

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A method for treating a subject with prostate cancer comprising:

(a) selecting for treatment a subject having prostate cancer wherein the subject has been HLA-typed and does not have an HLA haplotype selected from DQB1-02 and CWO7, and (b) administering to that subject, for a period of time, a MUC-1-based formulation, wherein the formulation comprises:

(i) a liposome; and (ii) at least one polypeptide comprising the amino acid sequence selected from the group consisting of the amino acid sequence of SEQ ID NO. 1 and the amino acid sequence of SEQ ID NO. 2.

2. The method of claim 1, wherein the formulation further comprises at least one adjuvant.

3. The method of claim 2, wherein the adjuvant is selected from the group consisting of lipid A, muramyl dipeptide, alum, a cytokine, and a combination thereof.

4. The method of claim 3, wherein the lipid A is monophosphoryl lipid A or a synthetic lipid A.

5. The method of claim 3, wherein the cytokine is interleukin-2.

6. The method of claim 1, further comprising a step (c) evaluating the treated subject.

7. The method of claim 6, wherein evaluating the treated subject comprises measuring an immune reaction in the treated subject.

8. The method of claim 7, wherein measuring the immune reaction in the treated subject comprises measuring a T-cell proliferation.

9. The method of claim 6, wherein evaluating the treated subject comprises determining at least one of: (a) tumor size, (b) tumor location, (c) nodal stage, (d) growth rate of the prostate cancer, (e) survival rate of the subject, (f) changes in the subject's lung cancer or prostate cancer symptoms, (g) changes in the subject's PSA concentration, (h) changes in the subject's PSA concentration doubling rate, or (i) changes in the subject's quality of life.

10. The method of claim 1, wherein the formulation is a BLP25 liposome vaccine comprising:

(c) a MUC-1 peptide comprising the sequence of SEQ ID NOS: 1 or 2;

(d) one or more adjuvants, and (e) one or more additional liposomal lipids.

11. The method of claim 10, wherein the BLP25 liposome vaccine is provided in a kit.

12. The method of claim 1, wherein the step of administering is by injection, aerosol, nasal, vaginal, rectal, buccal, occular, local, topical, intracisternal, intraperitoneal, or oral delivery, and wherein the injection is an intramuscular, intravenous, subcutaneous, intranodal, intratumoral, intraperitoneal, or intradermal injection.

13. The method of claim 1, wherein the period of time is selected from the group consisting of at least about 2 weeks, at least about 4 weeks, at least about 8 weeks, at least about 16 weeks, at least about 17 weeks, at least about 18 weeks, at least about 19 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, at least about 60 weeks, at least about 68 weeks, at least about 72 weeks, at least about 80 weeks, at least about 88 weeks, at least about 96 weeks, and at least about 104 weeks.

14. The method of claim 1, wherein the individual is treated with cyclophosphamide prior to (b).

15. The method of claim 1, further comprising calculating a combined score of the subject's physical well-being, functional well-being, and lung cancer or prostate cancer symptoms before, during, and after the period of time wherein the subject had been diagnosed with prostate cancer.

16. The method of claim 1, wherein the period of time is at least about 6 months, at least about 12 months, at least about 18 months, at least about 24 months, or longer than 24 months.

17. The method of claim 10, wherein the amount of MUC-1 peptide is about 300 μg.

18. The method of claim 10, wherein the adjuvant is lipid A.

19. The method of claim 18, wherein the amount of lipid A is about 150 μg.

20. The method of claim 10, wherein the amount of additional liposomal lipids is about 15 mg.

21. The method of claim 10, wherein the MUC-1 peptide comprises the sequence depicted in SEQ ID NO: 1.

22. The method of claim 10, wherein the MUC-1 peptide comprises the sequence depicted in SEQ ID NO: 2.

23. The method of claim 21, wherein the MUC-1 peptide is lipidated.

24. The method of claim 1, wherein the subject has rising PSA post-radical prostatectomy.

* * * * *

SEQUENCE LISTING

```
<160> NUMBER OF SEQ ID NOS: 3

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Thr Ala Pro Pro Ala His Gly Val Thr Ser Ala Pro Asp Thr Arg
 1               5                  10                  15

Pro Ala Pro Gly Ser Thr Ala Pro Pro
            20                  25


<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)
<223> OTHER INFORMATION: Lys-palmitoyl

<400> SEQUENCE: 2

Ser Thr Ala Pro Pro Ala His Gly Val Thr Ser Ala Pro Asp Thr Arg
 1               5                  10                  15

Pro Ala Pro Gly Ser Thr Ala Pro Pro Lys Gly
            20                  25


<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Thr Ala Pro Pro Ala His Gly Val Thr Ser Ala Pro Asp Thr Arg
```

-continued

```
1               5                   10                  15

Pro Ala Pro Gly
            20
```